United States Patent [19]

Ecanow

[11] Patent Number: 4,963,367
[45] Date of Patent: Oct. 16, 1990

[54] DRUG DELIVERY COMPOSITIONS AND METHODS

[75] Inventor: Bernard Ecanow, Wilmette, Ill.

[73] Assignee: Medaphore, Inc., Wilmette, Ill.

[21] Appl. No.: 130,550

[22] Filed: Dec. 15, 1987

Related U.S. Application Data

[63] Continuation-in-part of Ser. No. 711,066, Mar. 12, 1985, abandoned, and Ser. No. 710,048, Mar. 11, 1985, abandoned, and Ser. No. 835,550, Mar. 3, 1986, Pat. No. 4,849,405, and Ser. No. 896,844, Aug. 14, 1986, abandoned, and Ser. No. 1,814, Jan. 8, 1987, Pat. No. 4,794,000, and Ser. No. 31,237, Mar. 26, 1987, Pat. No. 4,914,084, and Ser. No. 54,193, May 26, 1987, abandoned, and Ser. No. 54,194, May 26, 1987, abandoned, and Ser. No. 811,675, Dec. 20, 1985, Pat. No. 4,738,952, which is a continuation-in-part of Ser. No. 604,476, Apr. 27, 1984, abandoned, said Ser. No. 835,550, is a continuation-in-part of Ser. No. 604,483, May 9, 1984, abandoned.

[51] Int. Cl.$^5$ .................. A61K 9/22; A61K 9/64; A61K 9/66; B01J 13/02
[52] U.S. Cl. .................. 424/485; 128/200.16; 264/4.1; 264/4.32; 264/4.7; 424/455; 424/460; 424/484; 424/485; 424/486; 428/402.2; 604/892.1
[58] Field of Search ............. 252/312; 264/4.1, 4.32, 264/4.7; 428/402.2; 514/78, 832, 833, 911, 963, 944, 959, 947, 965, 975; 128/200.16; 604/892.1; 424/485, 486, 455, 460, 484

[56] References Cited

U.S. PATENT DOCUMENTS

| | | | |
|---|---|---|---|
| 2,897,119 | 7/1959 | Dunn | 514/168 X |
| 2,913,342 | 11/1959 | Cameron et al. | 426/103 X |
| 3,190,837 | 6/1965 | Brynko et al. | 264/4.32 |
| 4,133,874 | 1/1979 | Miller et al. | 424/450 |
| 4,247,406 | 1/1981 | Widder et al. | 252/62.53 |
| 4,331,654 | 5/1982 | Morris | 514/78 X |
| 4,357,259 | 11/1982 | Senyei et al. | 264/4.3 |
| 4,397,870 | 8/1983 | Sloviter | 514/832 X |
| 4,485,045 | 11/1984 | Regen | 264/4.7 X |
| 4,746,508 | 5/1988 | Carey et al. | 424/88 |
| 4,761,288 | 8/1988 | Mezei | 514/944 X |
| 4,787,888 | 11/1988 | Fox | 604/892.1 X |

OTHER PUBLICATIONS

Karow, Jr. et al., "Organ Preservation for Transplantation", Little, Brown & Co., Boston, 1974, pp. 239–245. [RD 126, K3].
"Liposomes", Edited by Marc J. Ostro, The Liposome Co., Princeton, N.J., Marcel. Dekker, Inc., New York, 1983, p. 298.

*Primary Examiner*—Richard D. Lovering
*Attorney, Agent, or Firm*—Marshall, O'Toole, Gerstein, Murray & Bicknell

[57] ABSTRACT

Drug delivery compositions yeild new and unexpected degrees of stabilization, solubilization and delivery of incorporated medicaments, drugs, or other physiologically-active compounds. The compositions enable administration of drugs and other medically useful compounds via a variety of routes. More particularly, a drug delivery system or composition including one or more monomeric or polymerized surface active agents allows for rapid dissolution and smooth liberation of any desired incorporated drug or combinations, and the method of preparing the drug composition. In one embodiment, the physiologically-active compound is encapsulated by a coacervate-derived film, and the finished product is suitable for transmucosal administration. Other formulations of this invention may be administered via inhalation, oral, parenteral and by transdermal and transmucosal routes.

45 Claims, No Drawings

DRUG DELIVERY COMPOSITIONS AND METHODS

CROSS REFERENCE TO RELATED APPLICATIONS

This application is a continuation-in-part of the following U.S. applications: Ser. No. 711,066 filed Mar. 12, 1985 and now abandoned; Ser. No. 710,048 filed Mar. 11, 1985 and now abandoned; Ser. No. 835,550, filed Mar. 3, 1986, now U.S. Pat. No. 4,849,405 which is a continuation-in-part of Ser. No. 604,483 filed May 9, 1984, now abandoned; Ser. No. 896,844 filed Aug. 14, 1986 and now abandoned; Ser. No. 001,814 filed Jan. 8, 1987 and now U.S. Pat. No. 4,794,000; Ser. No. 031,237, filed Mar. 26, 1987 now abandoned; Ser. No. 054,193 filed May 26, 1987 and now abandoned; Ser. No. 054,194 filed May 26, 1987 and now abandoned; and Ser. No. 811,675 filed Dec. 20, 1985, now U.S. Pat. No. 4,738,952, which is a continuation-in-part of application Ser. No. 604,476 filed Apr. 27, 1984, now abandoned.

FIELD OF THE INVENTION

The present invention relates to a stable drug delivery composition in oral dosage form or capable of new and unexpected stabilization, solubilization and delivery of stable drug components in parenteral form at the pH of body tissue. More particularly, the present invention is directed to a drug delivery system or composition that allows for rapid dissolution and smooth liberation of any desired drug either orally or parenterally without precipitation, and the method of preparing the drug composition. In accordance with one embodiment of the present invention, liposomes and their contents can be enveloped in a coacervate-based film to prevent disintegration of liposome vehicles.

BACKGROUND OF THE INVENTION

Drugs now in common use often require formulation compromises in order to prepare the marketed product. Thus, many parenteral compositions must be prepared using the salt of the parent compound and an excessive pH.

The instability of many useful drugs and other useful medical compositions poses other formulation problems. At present, emulsions, microemulsions and liposomes constitute the principal approaches to these problems. While such dosage forms are an advance over older forms, they are often associated with erratic bioavailability and instability of their own.

The herein disclosed invention comprises a method to prepare compositions and compositions which deliver medically useful compositions effectively. The method is based upon the use of a non-toxic aqueous coacervate; said method produces stable microemulsions comprised of particles in which one or more pharmaceutical components have been incorporated. Through the process of this invention particles are enveloped by a coacervate-based film. The compositions of this invention may be administered orally, parenterally or by tissue absorption, as required.

The disclosed method enables the preparation of particles of any desired size and any degree of particle surface film hardness, any number of coacervate-derived films of any desired thickness, or any combination of particle sizes and surface hardnesses. In preferred compositions prepared by the disclosed invention, the particle size is about 1 micron or less. The pharmaceutical component(s) may be any water soluble or water insoluble medically useful composition or combinations of such compositions.

The inventor has previously disclosed compositions based on a coacervate system using albumin and lecithin as principal components of the system. However, by polymerizing one or both of these components, the inventor has not only simplified the method but unexpectedly produced a preparation with vastly improved encapsulating capability. Details of this improvement are presented in the Experiments Section.

DESCRIPTION OF THE PRIOR ART

While there are apparent similarities to the inventor's prior art, this application differs significantly in several important aspects. Thus, encapsulation is a fundamental aspect of the inventor's prior art and the present invention. However, by polymerizing one or more of the surfactants used in the present invention, and/or by modifying the previously disclosed processes, the proportion of the pharmaceutical component incorporated in the present formulation is approximately two to six times greater than that of formulations disclosed earlier.

The intravenous delivery of many pharmaceutical preparations has been limited to the use of aqueous singular systems, as discussed, based upon the salt of a parent compound and/or the dissolution of the compound by agents such as a propylene glycol or alcohol. Other known systems which function primarily as blood substitutes, however, are able to solubilize and deliver drugs infused therein to a restricted degree. U.S. Pat. No. 4,343,797 discloses a method of preparing a synthetic blood substitute based upon a two-phase heterogeneous physico-chemical system which provides for oxygen transport and other physiological functions inherent to whole natural blood. In U.S. Pat. No. 4,439,424 a preferred synthetic blood composition comprises albumin, water, sodium chloride, urea and lecithin in the form of a two-phase coacervate system which is rendered isotonic with human blood by the addition of controlled amounts of the sodium chloride. U.S. Pat. Nos. 4,558,032, 4,539,204 and 4,596,778 relate to gelatin based synthetic blood substitutes based upon a two-phase coacervate system utilizing respectively, gelatin and acacia; two gelatins; modified fluid gelatins of different isoelectric points; and gelatin or modified gelatin and lecithin. U.S. Pat. No. 4,547,490 discloses a further coacervate synthetic blood derived from an aqueous solution containing albumin, sodium chloride and lecithin in a nonpolar or semipolar solvent.

These known products have been found to be capable of carrying drugs, but have been designed to serve as a resuscitative fluid much in the manner of whole natural blood. One of the principal formulation problems successfully addressed by the aforementioned patents is maintenance of the structure and integrity of the microparticles (synthocytes) which comprise the composition.

The hemoglobin component of this composition (i.e., stroma-free hemoglobin, pyridoxilated-polymerized hemoglobin, liposome encapsulated hemoglobin and the like) remains functional and encapsulated within the microparticles (synthocytes) until the particles are metabolized and eliminated from the body. Encapsulation of the hemoglobin component not only preserves functionality but reduces or eliminates endotoxic reactions associated with non-encapsulated hemoglobin. The term "synthocyte" as used in this specification refers to the microparticles of this invention, the particles being about 1 micron or less in any single dimension when administered parenterally, and comprised of a coacervate-based matrix which contains the active component(s); and a coacervate-based film which envelopes the contents of the microparticle and constitutes the outer surface of the particle. The enveloping film may be comprised of one or more layers as required to prepare the desired composition. In this specification the terms "particle", "synthocyte" and "microparticle" will be used interchangeably.

Another example of a coacervate-based system is disclosed in International application No. PCT/US85/00859, published Nov. 21, 1985, relating to an oral dosage composition and method of preparation to enable the oral administration of insulin. The problems addressed by the disclosed coacervate system, however, include the need for protection of the insulin against degradation by enzymes, and factors such as the acid-base balance and other gastrointestinal conditions and processes. The coacervate-based film envelopes each individual insulin molecule to inhibit the interaction between the insulin component and the degrading conditions.

The prior art describing the liposome technology includes the following: The Ash and Hider U.S. Pat. No. 4,448,765 filed July 3, 1979 entitled LIPOSOMES AND THEIR USE IN TREATING HUMAN OR OTHER MAMMALIAN PATIENTS, describes microvesicles which are reportedly stabilized by the incorporation of a polymer having at least six atoms attached to the backbone thereof; said vesicles incorporating a physioplogically-active substance. Kelly U.S. Pat. No. 4,356,167 entitled LIPOSOME DRUG DELIVERY SYSTEMS, filed June 22, 1981, describes a liposome medicament delivery system wherein the medicament is in an aliphatic liquid-sterol-water lamellae. The lipid may be a sodium or potassium salt of a $C_4$ to $C_{18}$ fatty acid and the sterol may be cholesterol. Kao, Y. and Loo, T., Pharmacological Disposition of Negatively Charged Phospholipid Vesicles in Rats, J. of Pharm. Sci. 59;11, 1980, pp. 1338–1343 contains a report of experiments which investigated the pharmacological disposition of four negatively charged phospholipid vesicles. Gregoriadis, G., the Carrier Potential of Liposomes in Biology and Medicine; N.E. J. of Med. Vol. 295, No. 13, 1976, describes the use of liposomes to carry a large variety of biologically interesting compositions including hormones, drugs, steroids, vitamins, viruses and other compositions such as histamine. Doucet, D., et al; Oxygen Binding of Artificial Erythrocytes, in Proceedings of Int. Soc. of Artif. Organs, 5, (Supp) 1981, pp. 392–395, describes the use of liposomes to incorporate a concentrated hemoglobin solution. Gaber, B., et al; Encapsulation of Hemoglobin in Phospholipid Vesicles, FEBS Letters, Vol. 153, 2, 1983, pp. 285–287, describes a method to encapsulate hemoglobin in phospholipid vesicles. Gruner, S., Novel Multilayered Lipid Vesicles: Comparison of Physical Characteristics of Multilamellar Liposomes and Stable Plurilamellar Vesicles, Biochemistry, 24, 1985, 2833–2842, discusses the effects of osmotic compression on the production of various liposome compositions; Szebeni, J. et al.; Encapsulation of Hemoglobin in Phospholipid Liposome; Characterization and Stability; Biochemistry; 24, 1985, 2827–2832, reports the encapsulation of hemoglobin in liposomes of different lipid composition. Blood Policy and Technology; Office of Technology Assessment, U.S. Congress, U.S. Government Printing Office, 1985, pp. 146–151, reports the methods of formulation and the difficulties encountered in using liposome based blood substitutes.

It is important to emphasize that liposomes differ from the coacervate preparations previously discussed and herein disclosed in mode of manufacture, and in physical and structural properties.

Coacervates are used in the preparation of the compositions of this invention. The inventor's pending U.S. patent applications based on coacervate compositions include the following: Ser. No. 591,774 filed Mar. 21, 1984 now abandoned.

The Ecanow et al application Serial No. 811,675, filed Dec. 20, 1985, now U.S. Pat. No. 4,738,952 describes a synthetic whole blood wherein the coacervate system is produced from lecithin dispersed in an aqueous solution containing albumin and sodium chloride; said system enabling a more effective use of the incorporated pyridoxilated-polymerized hemoglobin.

The Ecanow application Serial No. 835,550, filed Mar. 3, 1986, now U.S. Pat. No. 4,849,405, describes an oral dosage form of insulin based on the use of a coacervate system comprised of lecithin, albumin, and insulin.

The Ecanow application Serial No. 711,066, filed Mar. 12, 1985, now abandoned, describes an oral dosage form of atrial peptides based on a coacervate comprised of lecithin, albumin, and atrial peptides.

The Ecanow application Serial No. 896,844, filed Aug. 14, 1986, and now abandoned describes a drug delivery system based upon an albumin-lecithin coacervate system using a solvent.

The Ecanow application Serial No. 001,814, filed Jan. 8, 1987, now U.S. Pat. No. 4,794,000 describes an oral drug delivery system based on a dextran-polyethylene glycol coacervate.

The Ecanow application Serial No. 006,620, filed Jan. 14, 1987, describes a composition useful for immunoassay procedures based upon an albumin-lecithin coacervate system.

There are fundamental differences between this invention and the inventor's prior art. In some instances, e.g., the blood substitute formulations, are based on precisely opposite theoretical and functional characteristics. Thus, the blood substitute formulations are based squarely on a gas exchange system. In this instance, oxygen is absorbed by the hemoglobin component of the synthocyte and released from the hemoglobin to the tissues according to oxygen tensions. This phenomena is represented in whole blood and some blood substitutes by a sigmoid curve. In contrast, in this invention, the drug is released from encapsulation; the release can be represented by a straight line function or by an exponential rate of release.

Further, the inventor's blood substitutes are specifically formulated to maintain the hemoglobin component in an encapsulated state up to the time the synthocyte and its contents are metabolized. In the present invention, the formulations are designed to release the drug from the synthocyte promptly after administration. The present invention provides for a variety of routes of administration; the inventor's blood substitutes are restricted to intravenous injection.

SUMMARY OF THE INVENTION

The method of this invention enables the preparation of carrier vehicles useful for the delivery of medically useful compositions for man and animals. The finished products of this invention range from a red blood cell substitute (resuscitation fluid) to aqueous based formulations of water insoluble, water soluble and water sensitive drugs.

The fact that in the method of this invention, aqueous formulations successfully incorporate and deliver water insoluble and water sensitive drugs is evidence that this invention constitutes a significant advance in the state of the art.

The aqueous based compositions of this invention comprise one or more of a large variety of surface active agents, that is, molecules which are non toxic and endogenous or exogenous to the body and can include one or more polymerized or polymerizable surface active agents, particularly a polymerized form of a protein such as albumin and/or a polymerized form of a phospholipid such as lecithin and may include one or more surface active agents either in polymeric or monomeric form, including lecithin, albumin, gelatin, modified liquid gelatin, acacia gel and combinations thereof. Finished products of this invention may be administered by oral, parenteral, transdermal, transmucosal or inhalation routes, or by combinations of these routes.

Formulations prepared according to the method of this invention are stable, pharmacologically-active and will not precipitate in body tissue or fluid. Parenteral drugs now prepared to an excessive pH can be reformulated using the method of this invention. The resulting product will have improved bioavailability and absorption; said reformulation will reduce or eliminate pain and tissue damage associated with injection of drugs with an excessive pH. The physiologically-active compounds, such as a drug, may be in a concentrated form, or may be dissolved or suspended in a carrier, e.g., a liquid carrier, such as an oil, glyceride, lipid, coacervate phase(s) or within a film carrier such as a liposome. In one embodiment, a liposome is encapsulated in a coacervate-based matrix or coacervate phase and/or coacervate-based film to prevent the liposome from unravelling prematurely.

Either prompt or sustained release characteristics or mixtures thereof, can be manufactured by the method of the present invention. The method of the present invention using a polymerized or polymerizable surface active agent constitutes an improvement in incorporating ability ranging from two to six times greater than that of the inventor's previously disclosed methods.

The delivery systems of this invention encompass emulsions, microemulsions, encapsulated liposomes, suspensions, gels and microsuspensions. The size of the coacervate-based encapsulated particles which comprise the finished products of this invention extend from the nanogram range to about one micron when administered parenterally. Larger size particles may be made by the disclosed method if required. Filtering procedures may be used to insure appropriate particle size. This invention envisages compositions in which particles 1 micron or less are mixed with particles 2 microns or more.

In this invention, the pharmacologically-active component is bound to or embedded in the coacervate matrix comprising the pharmacologically-active compounds held in a coacervate matrix of the equilibrium water phase and/or the coacervate phase forming a particle; and the particle, including the pharmacologically-active component and equilibrium water and/or coacervate phase (forming the coacervate matrix) is then encapsulated by a coacervate-based film. The coacervate-based film can contain one or more pharmacologically-active component(s), and layered films can contain no, or different, pharmacologically-active components. The film can be prepared to any degree of structure (hardness) ranging from soft (semi-gel like) to rigid. The method provides for a mixture of particle sizes if desired, and for any degree of surface film hardness, any number of surface films with or without an active compound, or combinations thereof.

OBJECTS OF THE PRESENT INVENTION

Accordingly, an object of the present invention is to provide a composition and a method of making the composition wherein one or more physiologically-active compounds are encapsulated by an aqueous coacervate-based film containing at least one polymerized surface active compound to provide unexpected stability to the composition.

Another object of the present invention is to provide a composition and a method of making the composition wherein one or more physiologically-active compounds is dissolved or dispersed in a liquid carrier and the carrier and compound are encased in an aqueous coacervate-based matrix containing at least one polymerized surface active compound, the composition including an aqueous colloid-rich phase or an aqueous colloid-poor phase or a combination of both phases from a two-phase coacervate system.

Another object of the present invention is to provide a composition and a method of making the composition wherein one or more physiologically-active compounds is dissolved or dispersed in a liquid carrier, such as a glyceride, and the carrier and compound are encased in an aqueous coacervate-based matrix containing at least one polymerized surface active compound including an aqueous colloid-rich phase or an aqueous colloid-poor phase or a combination of both phases from a two-phase coacervate system, thereby preventing the compound from diffusing out of the composition prematurely, and to prevent degradation of the compound by body fluids.

Another object of the present invention is to provide a method of administering a physiologically-active compound to a mammal wherein the composition includes one or more physiologically-active compounds in concentrated form or in a solid or liquid carrier, held in an aqueous coacervate-based matrix containing at least one polymerized surface active compound, surrounded or encapsulated with a film containing an aqueous colloid-rich coacervate phase.

Still another object of the present invention is to provide a composition and a method of making the composition wherein previously encapsulated physiologically-active compounds, such as compounds encapsulated in a liposome, are further stabilized by encapsulation in an aqueous coacervate-based matrix containing at least one polymerized surface active compound to prevent the compound from leaking by preventing the liposome from unravelling prematurely.

A further object of the present invention is to provide a composition and a method of making the composition wherein one or more physiologically-active compounds are encapsulated in an aqueous coacervate-based matrix containing at least one polymerized surface active compound, the matrix including a colloid-rich or a colloid-poor phase, or a combination of a colloid-rich and a colloid-poor phase to stabilize the physiologically-active compound and prevent the compound from prematurely leaking out of the matrix and to prevent compound-degenerative materials, such as enzymes, or digestive fluids, from reaching and degenerating the compound.

Another object of the present invention is to provide a composition and method of making the composition wherein one or more physiologically-active compounds are encapsulated by an aqueous coacervate-based matrix containing a polymer of lecithin to substantially and unexpectedly increase the yield or amount of physiologically-active compound capable of being carried in the composition.

Another object of the present invention is to provide a coacervate matrix enveloping one or more physiologically-active compounds wherein the coacervate matrix includes a plurality of surface active compounds one of which is polymerized albumin or polymerized lecithin.

The above and other objects and advantages of the present invention will become apparent from the following detailed description of the preferred embodiments.

DETAILED DESCRIPTION OF THE PREFERRED EMBODIMENTS

The present invention provides for a stable drug delivery composition useful for incorporating drugs, biologicals, peptides, enzymes, vitamins, nutrients and other medically useful compounds and compositions and for the stabilization, solubilization and delivery of pharmacologically-active substances. In one embodiment, the compositions of the present invention are derived from a non-toxic two-phase aqueous coacervate system forming a matrix containing at least one polymerized surface active compound, one phase of which is colloid-rich, semipolar to nonpolar in character and capable of solubilizing (holding within the coacervate matrix) oil-soluble and water-insoluble components (coacervate phase); the second phase of the coacervate composition is colloid-poor, semipolar to polar in character and capable of solubilizing (holding within the coacervate matrix) water-soluble and, to a lesser degree, water-insoluble compositions (equilibrium water phase). The polar phase of a coacervate composition is made of strong, dipolar molecules having hydrogen bonding, with dipole moments generally in the range from about 0.8D to about 1.85D. The semipolar phase is made up of strong, dipolar molecules that do not form hydrogen bonds, with dipole moments generally in the range from about 0.1D to about 0.8D. The nonpolar phase is made up of molecules have little or no dipole character, generally in the range of 0 to 0.1D. See Remington's Pharmaceutical Sciences, Mack Publishing Company, 1973, pp. 241-242. To a limited degree, however, the colloid-poor phase may be able to solubilize some apparently water-insoluble compounds, the colloid-rich phase being insoluble and in equilibrium with said colloid-poor phase. In this invention, a drug is incorporated in the coacervate phase based matrix and encapsulated comprises a medically useful, surprisingly stable composition suitable for oral, parenteral, transdermal, transmucosal or inhalation administration or combinations of such modes of administration.

As used in this invention the term, "transmucosal" means that a formulation of this invention is applied directly to any of the accessible mucosal membraneous tissues of the body. The term, "transdermal" is used to mean a formulation applied directly to the surface of the skin. Tissue absorption includes both transdermal and transmucosal modes of administration. The terms, "oral", "parenteral" and "inhalation" are used as per conventional definitions. In this invention, the oral route means that any oral dosage form can be accommodated, i.e., tablets, capsules, liquids, particles, and the like.

The term "drug" is defined by the Federal Food, Drug and Cosmetic Act, and as used in the present disclosure, is "articles recognized in the official *United States Pharmacopoeaia,* offical *Homeopathic Pharmacopoeaia,* or official *National Formulary* or any supplement to any of them". Further clarification of this definition is supported by *Remington's Pharmaceutical Sciences,* which states "drug" to mean "any article contained in the above-cited references which is used in the process of diagnosis, cure, treatment, mitigation or prevention of disease in man and animals". *Remington's Pharmaceutal Sciences,* (Easton, Pa.: Mack Publishing Co., 1975), p. 1843. All drugs as encompassed by any of these definitions can be incorporated into the coacervate compositions of the present invention for oral or parenteral administration to mammals.

It is known that the active components of many parenteral drugs such as antibiotics, anesthetics, anticancer agents, hypertensive compounds, and the like, are insoluble or only slightly soluble at the pH of plasma or tissue fluids and as such, the procedures commonly employed to deal with this problem include use of the salt of the parent compound and/or use of propylene glycol and/or alcohol as a solubilizing agent(s) for the drug. *Physician's Desk Reference,* (Oradell, N.J.: Medical Economic Co., 1986).

*U.S. Pharmacopoeaia,* indicates that of the injectable drugs used in the direct medical treatment of diseased states, approximately 200 are prepared from the salt of the parent compound and administered at a pH which differs significantly from that of body tissue. It follows from accepted pharmaceutic principles that when a drug based upon the salt of a parent compound is injected, the intracellular and extracellular water at the site of injection will buffer the drug sufficiently to alter its pH and cause a quantity of it to precipitate out of solution and into the injected site.

The following list illustrates the extensive use of the salt of the parent compound in injectable drugs as well as the frequency of an associated excessive pH. As is evident, virtually all classes of drugs are represented, and, in accordance with the principles of the present invention, are suitable for formulation in all embodiments of the coacervate compositions of the present invention for oral or parenteral administration or for tissue absorption.

| DRUG | pH |
|---|---|
| Acetazolamide, Sodium | 9.0–10.0 |
| Alphaprodine HCl | 4.0–6.0 |
| Amicocaproic Acid | 6.0–7.6 |
| Aminosuppurate Sodium | 6.7–7.6 |
| Aminophylline | 8.6–9.0 |
| Aminotryptyline HCl | 4.0–6.0 |
| Amobarbitol Sodium | 9.6–10.4 |
| Anileridine | 2.5–3.0 |
| Amphotericin B | 7.2–8.0 |
| Ampicillin | 5.0–7.0 |
| Anti coagulant Heparin Solution | 5.0–7.0 |
| Arginine HCl | 5.0–6.5 |
| Atropine Sulfate | 3.0–6.5 |
| Atrial Peptides | |
| Azathioprine Sodium | 9.8–11.0 |
| Benztropine Mesylate | 5.0–8.0 |

-continued

| DRUG | pH |
|---|---|
| Betaine HCl | 0.80–1.2 |
| Betamathazone Sodium | 8.0 |
| Bethanecol Chloride | 5.5–7.5 |
| Biperiden Lactate | 4.8–5.8 |
| Bleomycin Sulfate | 4.5–6.0 |
| Brompheniramine Maleate | 5.8–7.0 |
| Bupivacaine-Epinephrine Injection | 3.3–8.5 |
| Bupivacaine HCl | 4.0–6.5 |
| Butabartitol Sodium | 10.0–11.2 |
| Butorphanol Tartrate | 3.0–5.5 |
| Caffeine-Soidum Benzoate Injection | 6.5–8.5 |
| Calcium Glueptate Injection | 5.6–7.0 |
| Calcium Levulinate | 6.0–8.0 |
| Carboprost Tromethiamine Injection | 7.0–8.0 |
| Cefamandole Sodium | 6.0–8.5 |
| Cefamandole Nafate | 6.0–8.0 |
| Caphazolin Sodium | 4.5–7.0 |
| Cafataxime Sodium | 4.5–65. |
| Ceftizoxime Sodium | 4.5–6.5 |
| Cephalothin Sodium | 4.5–8.0 |
| Caphaprin Sodium | 6.5–8.0 |
| Caphradine | 8.0–9.6 |
| Cafonocid Sodium | — |
| Chloramphenicol | 5.0–8.0 |
| Chlordiazepoxide HCl | 2.5–3.5 |
| Chloroprocaine HCl | 2.7–4.0 |
| Chlorothiazide Sodium | 9.2–10.0 |
| Chlorpromazine HCl | 3.0–5.0 |
| Cefoperazone Sodium | 4.5–6.5 |
| Chlorphenramine Maleate | 4.0–5.2 |
| Chloroquine HCl | 5.5–6.5 |
| Chlortetracycline NCl | 2.3–3.3 |
| Clorprothixene | 4.0–5.0 |
| Colchicine Desmopressin | 6.0–7.0 |
| Clindamycin Phosphate | 5.5–7.7 |
| Cimetadine Hydrochloride | 4.0–6.0 |
| Codeine Phosphate | 3.0–6.0 |
| Corticotropin | 2.5–6.0 |
| Cyanocobalamin | 4.5–7.0 |
| Cyclizine Lactate | 3.2–4.7 |
| Cyclophosphamide | 3.9–6.7 |
| Cyclosporine | — |
| Cysteine HCl | 1.0–2.5 |
| Chlorprothixene HCl | 3.4 |
| Dantrolene Sodium | 9.5 |
| Dacarbazine | 3.0–4.0 |
| Cactinomycin | 5.5–7.5 |
| Daunorubicin HCl | 4.5–6.5 |
| Deslanoside | 5.5–7.0 |
| Desmopressin Acetate | 3.0–5.0 |
| Dexamethasone Sodium Phosphate | 7.0–8.5 |
| Diatrizoate Meglumine | 6.0–7.7 |
| Diatrizoate Sodium | 4.5–7.5 |
| Diazepam | 6.2–6.9 |
| Diazoxide | 11.2–11.9 |
| Dibucaine HCl | 4.5–7.0 |
| Dicyclomine HCl | 5.0–5.5 |
| Diethylstilbesterol Diphosphate | — |
| Digoxin | — |
| Dihydroergotamine Mesylate | 3.2–4.0 |
| Diphenhydramine HCl | 4.0–6.5 |
| Dimenhydrinate | 6.4–7.2 |
| Dobutamine HCl | 2.5–5.5 |
| Dopamine HCl | 2.5–5.5 |
| Dopamine HCl-Dextrose | 3.0–5.0 |
| Doxapram HCl | 3.5–5.0 |
| Doxorubicin HCl | 3.8–6.5 |
| Droperidol | 3.0–3.8 |
| Dhphylline | 5.0–8.0 |
| Edetate Disodium | 6.5–7.5 |
| Emetine HCl | 3.0–4.0 |
| Ephedrine Sulfate | 4.5–7.0 |
| Epinephrine | 2.5–5.0 |
| Ergonovine Maleate | 2.7–3.5 |
| Ergotamine Tartrate | 3.0–4.0 |
| Erythromycin | — |
| Erythromycin Ethylsuccinate | 6.0–8.5 |
| Erythromycin Gluceptate | 6.0–8.0 |
| Erythromycin Lactibionate | 6.5–7.5 |
| Estradiol Valerate | — |
| Ethacrynate Sodium | 6.3–7.7 |

-continued

| DRUG | pH |
|---|---|
| Ethylnorepinephrine HCl | 2.5–5.0 |
| Etidocaine HCl | 11.0 |
| Fentanyl Citrate | 4.0–7.5 |
| Floxuridine | 4.0–5.5 |
| Fluorescein Sodium | 8.0–9.0 |
| Fluoracil | 8.6–9.0 |
| Fluphenazine Enanthate | — |
| Fluphenazine HCl | 4.8–5.2 |
| Folic Acid | 8.0–11.0 |
| Furosemide | 8.5–9.3 |
| Fallamine Triethiodide | 5.3–7.0 |
| Gentamycin Sulfate | 3.0–5.5 |
| Glucagon | 2.5–3.0 |
| Glycopyrrolate | 2.0–3.0 |
| Haloperidol | 3.0–3.8 |
| Heparin-Calcium | 5.0–7.5 |
| Heparin-Sodium | 5.0–7.5 |
| Hetacillin-Potassium | 7.0–9.0 |
| Hexafluorenium Bromide | 4.0–7.0 |
| Histamine Phosphate | 3.0–6.0 |
| Hyaluranidase | 6.4–7.4 |
| Digitoxin | — |
| Fructose | 3.0–6.0 |
| Hydralazine HCl | 3.4–4.4 |
| Hydrocortisone Sodium Phosphate | 7.5–8.5 |
| Hydrocortisone Sodium Succinate | 7.0–8.0 |
| Hydromorphone HCl | 4.0–5.0 |
| Hydoxocobalamin | 3.5–5.0 |
| Hydroxyzine HCl | 3.5–6.0 |
| Hyoscyamine Sulfate | 3.0–4.5 |
| Imipramine HCl | 4.0–5.0 |
| Iophendylate | 6.5–7.7 |
| Iothalamate Sodium | 6.5–7.7 |
| Iron Dextran | 5.2–6.5 |
| Isobucaine HCl-Epinephrine | — |
| Isoniazid | 6.0–7.0 |
| Isoproterenol HCl | 3.5–4.5 |
| Isoxsuprine HCl | 4.9–6.0 |
| Kanamycin Sulfate | 3.5–5.0 |
| Ketamine HCl | 3.5–4.5 |
| Leucovorin Calcium | 6.5–8.5 |
| Levallorphan Tartrate | 4.0–4.5 |
| Lidocaine HCl | 5.0–7.0 |
| Lidocaine HCl Dextrose | 3.5–7.0 |
| Lidocaine HCl-Epinephrine | 3.3–5.5 |
| Lidocaine HCl-Epinephrine Bitartrate | 3.3–5.5 |
| Lincomycin HCl | 3.0–6.6 |
| Magnesium Sulfate | 5.5–7.0 |
| Magnesium Chloride | 1.5–2.5 |
| Methlorethamine HCl | 3.0–5.0 |
| Menotropins | 6.0–7.0 |
| Meperidine HCl | 3.5–6.0 |
| Mephentermine Sulfate | 4.0–6.5 |
| Mepivacaine HCl | 4.5–6.8 |
| Mepivacaine HCl-Levonordefrin | 3.3–5.5 |
| Meprylcaine HCl-Epinephrine | 3.5–5.5 |
| Mesoridazine Besylate | 4.0–5.0 |
| Metaraminol Bitartrate | 3.2–4.5 |
| Methadone HCl | 3.0–6.5 |
| Methicillin Sodium | 5.0–7.5 |
| Methiodal Sodium | 5.0–8.0 |
| Methocarbamol | 3.5–6.0 |
| Methohexital Sodium | 10.6–11.6 |
| Methotrexate Sodium | 8.0–9.0 |
| Methotrimeprazine | 3.0–5.0 |
| Methoxamine HCl | 3.0–5.0 |
| Methscopolamine Bromide | 4.5–6.0 |
| Methyldopate HCl | 3.0–4.2 |
| Methylergonovine Maleate | 2.7–3.5 |
| Methylpredisolone Sodium Succinate | 7.0–8.0 |
| Metronidazone | 4.5–7.0 |
| Miconazole | 3.7–5.7 |
| Minocycline HCl | 2.0–3.5 |
| Mitomycin | 6.0–8.0 |
| Morphine Sulfate | 2.5–6.0 |
| Moxalactam Disodium | 4.5–7.0 |
| Nafcillin Sodium | 6.0–8.5 |
| Naloxone HCl | 3.0–4.5 |
| Neostigmine Methylsulfate | 5.–6.5 |
| Netilmicin Sulfate | 3.5–6.0 |
| Niacin | 4.0–6.0 |

| DRUG | pH |
| --- | --- |
| Niacinamide | 5.0–7.0 |
| Norepinephrine Bitartrate | 3.0–4.5 |
| Nylidrin HCl | 4.5–6.5 |
| Orphenadrine Citrate | 5.0–6.0 |
| Oxacillin Sodium | 5.0–8.5 |
| Oxymorphone HCl | 2.7–4.5 |
| Oxytetracycline | 8.0–9.0 |
| Oxytetracycline HCl | 2.0–3.0 |
| Oxytocin | 2.5–4.5 |
| Papaverine HCl | 3.0 or less |
| Parathyroid | 2.5–3.5 |
| Penicillin G Potassium | 6.5–8.5 |
| Penicillin G Procaine | 5.0–7.5 |
| Penicillin G Sodium | 6.5–7.5 |
| Pentazocine Lactate | 4.0–5.0 |
| Phenobarbital Sodium | 9.0–10.5 |
| Perphenazine | 4.2–5.6 |
| Phenobarbital Sodium | 9.0–10.5 |
| Perphenazine | 4.2–5.6 |
| Phenobarbitol Sodium | 9.2–10.2 |
| Phentolamine Mesylate | 4.5–6.5 |
| Phenylephrine HCl | 3.0–6.5 |
| Phenytoin Soidum | 10.0–12.3 |
| Physopstigmine Salicylate | 4.0–6.0 |
| Phytonadione | 3.5–7.0 |
| Plicamycin | 5.0–7.5 |
| Posterior Pituitary | 2.5–4.5 |
| Potassium Acetate | 5.5–8.0 |
| Potassium Chloride | 4.0–8.0 |
| Prednisolone Sodium Phosphate | 7.0–8.0 |
| Prednisolone Sodium Succinate | 5.7–8.0 |
| Prilocaine HCl | 5.0–7.0 |
| Procainamide HCl | 4.0–6.0 |
| Procaine HCl | 3.0–5.5 |
| Procaine HCl-Epinephrine | 3.0–5.5 |
| Procaine-Phsnylephrine Hydrochlorides | 3.0–5.5 |
| Procaine and Tetracaine HCl and Levonodefrin | 3.5–5.0 |
| Prochlorperazine Edisylate | 4.2–6.2 |
| Promazine HCl | 4.0–5.5 |
| Promethazine HCl | 4.0–5.5 |
| Propiomazine HCl | 4.7–5.3 |
| Propoxycaine-Procaine HCl's-Norepinephrine Bitartrate | 3.5–5.0 |
| Propanolol HCl | 2.8–4.0 |
| protein Hydrolysate | 4.0–7.0 |
| Pyridostigmine Bromide | 4.5–5.5 |
| Pyridoxine HCl | 2.0–3.8 |
| Quinidine Gluconate | — |
| Reserpine | 3.0–4.0 |
| Riboflavin | 4.5–7.0 |
| Ritodrine HCl | 4.8–5.5 |
| Rolitetracycline | 3.0–4.5 |
| Scopolamine HCl | 3.5–6.5 |
| Secobarbital Sodium | 9.0–10.5 |
| Sisomycin Sulfate | 2.5–5.5 |
| Spectinomycin HCl | 3.8–5.6 |
| Streptomycin Sulfate | 5.0–8.0 |
| Succinylcholine Chloride | 3.0–4.5 |
| Sulfadizazine Sodium | 8.5–10.5 |
| Sulfixoxazole Diolamine | 7.0–8.5 |
| Superoxide Dismutase | — |
| Terbutaline Sulfate | 3.0–5.0 |
| Testosterone Cypionate | — |
| Testosterone Enanthate | — |
| Tetracaine HCl | 3.2–6.0 |
| Tetracycline HCl | 2.0–3.0 |
| Tetracycline Phosphate Complex | 2.0–3.0 |
| Thiamine HCl | 2.5–4.5 |
| Thimylal Sodium | 10.7–11.5 |
| Thiethylperazine Maleate | 3.0–4.0 |
| Thiopental Sodium | 10.2–11.2 |
| Thiothixene HCl | 2.5–3.5 |
| Tobramycin Sulfate | 6.0–8.0 |
| Tolazoline HCl | 3.0–4.0 |
| Tolbutaminde Sodium | 8.0–9.0 |
| Triamcinolane Diacetate | 6.0 |
| Tridihexethyl Chloride | 5.0–7.0 |
| Trifluoperazine HCl | 4.0–5.0 |
| Triflupromzine HCl | 3.5–52. |
| Trimethaphan Camsylate | 4.9–5.6 |
| Trimethobenzamide HCl | 4.8–5.2 |
| Trimethoprimsulfamethoxazole | 10.0 |
| Tromethamine | 10.0–11.5 |
| Tubocurarine Chloride | 2.5–5.0 |
| Vasopressin | 2.5–4.5 |
| Vincristine Sulfate | 3.5–4.5 |
| Vidarabine Concentrate | 5.0–6.2 |
| Vinclastine Sulfate | 3.5–5.0 |
| Warfarin Sodium | 7.2–8.3 |
| Verapamil | 4.1–6.0 |

It is to be understood that the above list of drugs is for purposes of illustration and is not provided as an all inclusive list of all the drugs which may be beneficially formulated or reformulated using the oral or parenteral drug, tissue absorptive, transmucosal, or inhalation delivery compositions of the present invention. Other physiologically-active compounds that can be encapsulated in the coacervate compositions of the present invention include biologically-active compounds, such as proteins, enzymes, anti-enzymes, peptides, catecholamines, anti-histamines, analgesics, and the like. For the purposes of the present invention "biological" is defined to mean any medically useful composition derived from a biological source and/or a synthetic pharmacological equivalent thereof such as insulin, heme, hemoglobin (bovine, human, or synthetic), and hormones; "enzyme" or "enzyme system" is defined to mean any protein or conjugated protein produced biologically or synthetically and which functions as a biocatalyst; "peptide" refers to peptides and polypeptides derived from either endogenous, exogenous, or synthetic sources and is used to mean polymers of amino acids linked together by an amide type linkage known as a peptide bond. Anti-enzymes are chemical or biological entities specific to a given enzyme which act to interfere with or terminate the biological activity of the enzyme. Other medically useful compositions known to those skilled in the art, for example, globulin, one or more glycoproteins, such as erythropoeitin, also may be incorporated in the compositions of the present invention.

Drug compounds dissolved in any non-toxic, physiologically-acceptable solvent such as a glycol, for example, propylene glycol, and/or alcohol also may be used in the practice of this invention. The procedure and quantity of drug incorporated when using such compositions are any desired quantity, such as that described.

The following are examples of standard doses which can be incorporated into the coacervate-based matrix-enveloped compositions or products of this invention:

| | |
| --- | --- |
| Cimetidine HCl | 150 mg/ml |
| Diazepam | 5 mg/ml |
| 5-Fluorouracil | 500 mg/10 ml |
| Erythromycin Lactobionate | 1 mg/ml |
| Flosuridine | 500 mg/5 ml |
| Amthoteracin D | 0.1 mg/ml |
| Fluphenazine HCl | 2.5 mg/ml |
| Heparin Sodium | 1,00–20,000 units/ml |
| Haloperidol lactate | 5 mg/ml |
| Insulin | 40 units |
| Ketamine HCl | 10 mg/ml |
| Labeltol HCl | 5 mg/ml |
| Lipocaine HCl | 10 mg/ml |
| Miconazole | 10 mg/inl |
| Morphine Sulfate | 0.5–1.0 mg/ml |
| Dropendal 2.5 mg/ml | |

-continued

| | |
|---|---|
| Imipramine HCl | 25 mg/2 ml |
| Phenytoin 100 mg/ml | |
| Pentobartital Sodium | 50 mg/ml |
| Tetracycline HCl | 250 mg/100 ml |
| Thiopental Sodium | 0.2 mg/2 ml |
| Verapamil HCl | 2.5 mg/ml |
| Vincristine Sulfate | 1.0 mg/ml |
| Fentanyl citrate | 0.05 mg/ml |
| Methylprednisolone Sodium Succinate | 40 mg/ml |

Once the drug is solubilized in (held within the matrix of) the colloid-rich phase of the composition of the present invention and adjustments are made to the pH, if necessary, e.g., to 7.3–7.4 by the addition, for example, of either hydrochloric acid or sodium bicarbonate, the preparation may be administered or stored in the standard or desired dose in appropriate containers such as ampules, vials, and the like. Alternatively, following solubilization of the drug in the coacervate phase, the previously separated colloid-poor phase can be added and the resulting mixture emulsified using techniques known to produce microemulsions. Following adjustment of the pH to, for example, 7.3–7.4, by adding either HCl or sodium bicarbonate as required, the preparation is now ready for use or storage. In some instances, as noted previously, the colloid-poor phase may be used to solubilize and prepare formulations of polar and semipolar drug compositions.

Other medically useful compositions encompassed by the definition of drugs herein are also delivered more effectively orally, parenterally or by other means of administration that eventuate in tissue absorption of the drug(s) by incorporation into the compositions of the present invention since such incorporation improves such parameters as stability, solubility, delivery and the like. Other medically useful compounds capable of being incorporated in the compositions of all embodiments of the present invention include vitamins, for example, vitamin B complex, vitamins A, D, E and K, vitamin $B_{12}$, folic acid, and the like. Additionally, enzymes such as glucagon, lipase, a-amylase, superoxide dismutase, and the like, and nutrients such as fats, proteins, amino acids and carbohydrates may be incorporated into the drug delivery compositions of the present invention. Nutritional formulations using the compositions of the present invention may include both water-soluble and water-insoluble compounds, for example, vitamins, polyunsaturated corn oil, soy oil, triglycerides, amino acids, soy protein isolate, soy lecithin, corn syrup, sucrose and other nutritional entities known to be useful when normal food intake is precluded or otherwise interfered with. Peptide and/or polypeptide compositions, particularly dipeptides and tripeptides, also can be included in the compositions of the present invention. Additional active compounds includeable into the coacervate compositions of the present invention, particularly for oral administration include Azothioprine; Cyclosprine; Monensin; low molecular weight Heparin, Amrinone and other ionotropics; Superoxide Dismutase; Protaglandins; Interferons; Urokinase; hGH (human growth hormone); Aminoglycoside antibiotics; Estrogens; Cephalosporins; Androgens; Anti-androgens; Renin Inhibitors; Lipoxygenase Inhibitors; Hypothalmic and Pituitary Hormones; Cardiac Glyscosides; Anti-inflamatory steroids; Non-steroid Inflammatory drugs; Vancomycin; Tissue Plasminogen Activators; Enzymes such as adenosine deaminase; and blood factors, such as Factor VIII and Factor IX complex.

Compositions of one embodiment of the present invention comprise one or more non-toxic surface active polymers which may be derived from endogenous, exogenous or synthetic sources. For purposes of this invention they may be selected from any of the classes of surfactants described by Zographi (Ref: Remington's Pharmaceutical Sciences, pp. 295-296, Mack Publishing Co. 1976). These polymers are obtained from the following monomers: anionic, cationic, amphoteric, and non-ionic surfactants. Surface active agents in the anionic classification include di-(2-ethylhexyl) sodium sulfosuccinate; non-ionic compositions include polyethylene glycol (PEG) and polymerized esters; and amphoteric surface active agents include (1) compounds classified as simple, conjugated, derived, and secondary proteins such as the albumins; gelatins; modified fluid gelatins; lipoproteins; alpha, beta and gamma globulins and glycoproteins, and (2) compounds referred to as phospholipids. The amine salts and the quaternary ammonium salts within the cationic group also comprise useful surfactants. Other surfactant compounds useful to form coacervates in accordance with the principles of the present invention include compositions within the groups known as the polysaccarides. and their derivatives, such as chitosan; dextran; the mucopolysaccarides; and the polysorbates and their derivatives. Synthetic polymers that may also be used include compositions such as polyethylene glycol and polypropylene glycol. Other suitable surface active agents that can be used to prepare coacervate compositions useful in accordance with the principles of the present invention include pectin, glycoprotein, glycolipid, galactose, and modified fluid gelatin. Acceptable coacervate compositions can be made from single surface active agents listed above or through the use of appropriate combinations thereof.

Compounds that are not intrinsically surface active may also be used to prepare coacervates provided they can be made surface active by chemical or other means. Thus, fatty acids are not considered to be surface active compounds; however, when they are reacted with an alkaline chemical entity, the resulting reaction products will include one that has surface active properties. For instance, mixing stearic acid with sodium hydroxide will produce a salt of stearic acid that has surfactant characteristics.

Virtually all surfactants useful to this invention can by polymerized (e.g., modified fluid gelatin) and used in the method and compositions of the present invention.

As noted above, known synthetic polymers, e.g., polyethylene glycol dextran, a polysaccaride, and the like, may be used in this invention.

To achieve the full advantage of the present invention, the coacervate matrix includes at least one polymerized surfactant. The polymerized surfactant or a combination of polymerized and monomeric surfactants have produced delivery systems that are exceptional in their ability to entrap hemoglobin and other pharmaceutical components.

Surfactants useful to this invention can be polymerized by using, as an example, any of the customary aldehydes (e.g., glutaraldehyde) and following known procedures associated with the use of the aldehydes to produce the polymer form.

To achieve the full advantage of the present invention, the combination of the surface active compounds include polymerized albumin and polymerized lecithin; polymerized albumin and monomeric lecithin; monomeric albumin and polymerized lecithin; casein and polymerized lecithin; gelatin and polymerized lecithin; pectin and polymerized albumin. It should be noted, however, that coacervate compositions useful in accordance with the principles of the present invention can be made from selected single surface active agents such as polymerized albumin or polymerized lecithin.

To achieve the full advantage of the present invention, one of the surface active agents should be a phospholipid, such as lecithin or polymerized lecithin, in the composition of the present invention. It may be derived from any suitable source. Egg lecithin is preferred. Other phospholipids such as cephalin, isolecithin, sphingomyelin, phosphatidyl serine, phosphatidic acid, phosphatidyl inositol and phosphatidyl choline, and combinations thereof, may be used in place of or in addition to lecithin, particularly where the other surfactant is polymerized albumin.

Further, to achieve the full advantage of the present invention, a suitable surface-active protein, such as albumin or polymerized albumin, comprises another component of the compositions of the present invention. Albumin derived from any acceptable source, such as human, is acceptable. Other suitable surface active proteins include alpha-, beta- and gamma-globulins, gelatin, modified fluid gelatin, lipoproteins, polypeptides and mucopolysaccharides. While albumin is preferred, any suitable, non-toxic protein, i.e., simple, conjugated or derived proteins or mixtures thereof, including the globulins may be used in place of albumin. When globulin is used in the process described in this specification, the finished product not only comprises a coacervate but a composition in which the medical usefulness and the activity of the gamma globulin is prolonged.

Applications of this invention used to prepare orally administered medications involve the use of compositions which have solvent properties but which also serve as a matrix or substrate for the incorporated drug(s) in these methods. These include glycerides such as mono, di, and triglycerides or any combination thereof, or commercial products such as KAOMEL, (manufacturer: Durkee, Cleveland, Ohio) esters of fatty acids such as methyl oleate or combinations of such esters, or waxes such as carnuaba wax or any appropriate combination of the above. In certain applications, volatile organic solvents may be used to place the drug component into solution, i.e., carbon tetrachloride, provided that such solvents are completely removed before the finished product is delivered. As is described in subsequent sections of this specification, the methods used to produce the orally administered compositions also serve as the basis for medications that are useful for transdermal, transmucosal or inhalation methods of administration or combinations thereof.

The use of an aqueous based coacervate composition as the starting composition for the microemulsions of the finished products of the present invention distinguishes the compositions of the disclosed invention from known microemulsions that are comprised of a lipid (liquid or solid) or oil phase and a water phase. It should be noted that stabilization of known microemulsions by encasing the microemulsions in a coacervate phase matrix and/or film, in accordance with the principles of the present invention, is an important feature of the present invention.

In accordance with another important embodiment of the present invention, liposomes and their contents are enveloped with a coacervate-based film—the film being derived from any of the two-phase liquid aqueous non-toxic coacervate compositions described herein. Liposomes of any acceptable composition and of any lamellar structure, i.e., unilamellar, multi-lamellar, or plurilamellar, or any combination may be used in accordance with the principles of this embodiment of the present invention. Further, the liposome may contain any of the following physiologically-active components: any oxygen carrying molecule or oxygen solvent(s), any drugs, hormones, biologicals, steroids, peptides, tissue plasminogen activators, enzymes, anti-enzymes and/or any other compositions or combinations thereof which are of biological or medical interest. Suitable oxygen solvents include perfluorocarbons; the coacervate phase of a lecithin-water coacervate solution; the coacervate phase of a lecithin-albumin-water solution, and the like. The source of the physiologically-active compound(s) can be either endogenous, exogenous or synthetic or any acceptable, non-toxic combination thereof.

The liposome embodiment of the present invention comprises a liposome component, the pharmaceutic and/or pharmacologic entity(s), or combinations thereof, contained within the liposomes, and a coacervate based matrix and/or film encapsulating the liposome component and its contents. In this embodiment of the present invention, liposomes containing the physiologically-active molecule are mixed into a surfactant solution such as a solution of polymerized albumin. To achieve the full advantage of this embodiment of the present invention, the surfactant (polymerized albumin) solution also contains polymerized lecithin and is converted to a coacervate phase to form a coacervate matrix and/or film enveloping the liposome composition.

Further emulsification of this mixture produces a composition enveloping the liposome in a coacervate-based matrix and/or film. The emulsified composition including the liposome enveloped by a coacervate-based matrix and/or film then is microemulsified to produce a microemulsion having particles of 1 micron or less in size. As an option, microemulsion(s) can be processed further to produce sustained release compositions; the methods include application of heat; use of a cross-linking agent, or repeating specific process steps.

As a further option, the composition may be dried, such as by treatment with heat, or freeze dried to produce a lyophilized product, which can be produced to any desired particle size and reconstituted with any physiologically appropriate fluid. When reconstituted, such compositions include a resuscitation fluid and a delivery system to introduce compositions of biological or medical interest into the body.

The specific compositions of this invention can be administered either parenterally, transdermally, orally, absorbed through the tissue lining of other body sites, or via inhalation, or combinations thereof, as appropriate.

When the reconstituted composition is intended for intravenous use, isotonicity and pH should be adjusted by known procedures to normal body values before administration. A single layer of coacervate matrix and/or film encapsulates the composition. If desired, in accordance with a preferred method, the finished product can be subjected to film encapsulation procedures repeatedly to produce concentric films of any desired thickness. Each film can contain no additional physiologically-active component or each can contain a desired concentration of any physiologically-active component, same or different.

While it is preferred that the microparticles of the finished products of this invention be 1 micron or less, particularly when administered parenterally, there are conditions, such as for oral administration, when microparticles of this invention are 2 microns or more in size.

In accordance with one embodiment of the present invention, any appropriate non-toxic coacervate composition containing one or more polymerized surface active agents, particularly polymerized albumin and/or polymerized lecithin can be used in the manufacture of the drug delivery compositions of the present invention. The coacervate-enveloped compositions of the present invention incorporate non-toxic endogenous or exogenous surface-active agents, derivatives thereof and/or combinations of surface-active agents or derivatives.

In the preferred formulation, polymerized albumin comprises one component. The lecithin that is used in this method may be monomeric or polymerized. One method by which lecithin can be polymerized is as follows: Remove one or both of the fatty acids of lecithin by hydrolysis. This step results in a free hydroxyl group on each lecithin molecule. This in turn produces a lecithin composition that lends itself to polymerization by customary techniques.

To achieve the full advantage of the present invention, the polymerized albumin should contain from two to six albumin molecules. Longer molecule chains may be used but are not preferred. To achieve the full advantage of the present invention, the weight average molecular weight of the polymerized albumin used in this invention should range from about 200,000 to about 300,000, preferably from about 200,000 to about 280,000. Compositions of greater or lesser molecular weight may also be used. The albumin component can be derived from any acceptable, endogenous, exogenous, or synthetic source including genetically engineered sources. The lecithin may be derived from any suitable non-toxic source. In the practice of this invention, any acceptable phospholipid can be substituted for lecithin. In such case the phospholipid may be monomeric or polymerized. To achieve the full advantage of the present invention, polymerized lecithin used in the method and compositions of the present invention contains three to four linked lecithin molecules and has a weight average molecular weight of about 1600 to about 3200, preferably about 2500. Shorter or longer chain phospholipids also may be used.

In preparing the red blood cell substitutes (resuscitation fluids), it is preferred that a reducing agent be added to the product in the process of manufacture.

Depending upon the finished product to be produced, the pharmaceutically-active component may be an oxygen carrying molecule, an oxygen solvent molecule, hormone(s), water soluble drugs) water insoluble drug(s), biological(s), a water sensitive drug(s), a peptide(s), an enzyme(s), and the like, either singly or in combination. The active component is incorporated in the composition during the manufacturing steps in that quantity that will provide the desired clinical amount. Thus, for example, in the case of drugs, this will be the dose given in the Physician's Desk Reference plus five to fifteen percent. If desired, greater or lesser amounts of any given drug may be used to meet specific medical requirements. In the case of the inclusion of hemoglobin, the preferred quantity is that amount that will produce fourteen percent hemoglobin in the finished product. Greater or lesser quantities of hemoglobin may also be used depending upon the end use of the finished product. If desired, a sterol, such as cholesterol, cholesterol, and/or urea preferably about 0.1% to 3% may be included in the composition to formulate red blood cell substitutes.

Any composition of this invention to be administered orally can be formulated to any dosage, e.g., capsules, tablets, syrups, emulsions, suspensions, microemulsions, and the like.

When preparing the intravenous red blood cell substitute of this invention, the basic method is followed. Additional steps are used, however, to adjust the pH, viscosity, and isotonicity of the preparation, when necessary, to approximate the values of whole human blood. In the method of this invention that prepares parenteral products, the pH is adjusted to approximately 7.4. The oral drug compositions of this invention require no adjustment of pH, viscosity or isotonicity pH adjustment, however, is preferred. Manufacture of all preparations of this invention are preferably made under sterile conditions.

To prepare the red blood cell substitute, the following method is used: to 100 mls of a 30% solution of monomeric lecithin, add 10 gms of stroma-free hemoglobin and, if desired, also add 0.1% cholesterol. If cholesterol is used first it should be dissolved into the surfactant, e.g. lecithin, such as with the aid of a solvent, e.g., n-butyl alcohol. The quantity of the hemoglobin component can vary from 1% w/v to 20% w/v. If desired, modified hemoglobin may be substituted in the same quantities for stroma-free hemoglobin. In addition, hemoglobin encapsulated within liposomes may be substituted for the preferred stroma-free hemoglobin. It is preferred that a reducing agent and/or an antioxidant such as reduced nicotinamide adenine dinucleotide phosphate (NADPH), or reduced nicatinamide adenine dinucleotide phosphate (NADH), or glutathione, or dextrose, or ascorbic acid or other known non-toxic antioxidants be added as the next step. Appropriate combinations of reducing agents also may be used, if desired. If added, such compounds are added in such quantity as will prevent the oxidation of the hemoglobin component; generally trace amounts up to about 3 molar percent based upon the molar amount of hemoglobin. To achieve the full advantage of the present invention, the reducing agent should be included in an amount of from trace amounts to 6 millimoles per mole of hemoglobin. Acceptable compositions may be prepared without the use of reducing agents.

Following this step add 20 gms of either monomeric or polymerized albumin. The polymerized form is preferred. The resulting composition then is processed by means of a colloid mill and/or a micro-fluidizer for about 10 minutes. During this processing step add a polymerization initiator, e.g., a solution of 1-ethyl-3-dimethyl-aminopropyl-carbodiimide of about 10% added during colloid milling and/or micro-fluidizing for in-situ polymerization of the albumin during processing of the composition. The quantity of polymerization initiator may range from about 0.1% to about 20% based on the total weight of the composition. Following this processing step the product is stored from about 4 to about 12 hours at a temperature that may range from about 4° C. to about 10° C. The internal phase (particles) are separated from the aqueous system by known filtering or separation means and washed with sterile saline solution. The particles then are dispersed in physiological saline solution.

The pH of the preparation is adjusted, if necessary, to approximate that of whole human blood. Addition of HCl or NaOH may be used for this purpose. Isotonicity of the product is adjusted, if necessary, to approximate that of whole human blood. This may be accomplished by the addition of appropriate amounts of any of the following: electrolytes present in human plasma, normal physiological saline solution, Ringer's solution, or any other suitable composition.

Next, adjust the viscosity of the product so that it approximates the viscosity of whole human blood, for example, by the addition of water to decrease the viscosity, or by adding any non-toxic, physiologically-acceptable hydrophillic colloid, such as albumin or pectin, to increase the viscosity. On completion of this step the product comprises a micro-emulsion that consists of microencapsulated particles containing the hemoglobin component. It should be emphasized that this method encapsulates hemoglobin more efficiently than that of the inventor's previously disclosed encapsulating techniques.

At this stage of manufacture the product may be used as a red blood cell substitute (resuscitation fluid) provided that it is first filtered to remove all extraneous matter and all particles that exceed 1 micron in size in any dimension.

It is preferred, however, that the filtered product be processed further using either a chemical process based on a crosslinking agent, such as glutaraldehyde, or a physical processing step such as heat. The heating step is preferred and consists of heating the preparation for about 2 minutes at a temperature that may range from about 50° C. to about 70° C. The duration of the heating step may be more than 2 minutes or less than 2 minutes depending upon the desired degree of particle(s) surface film structuring. While temperatures less than 50 degrees Centigrade are feasible for this purpose, they are not preferred. A combination of crosslinking and heating for film hardening also can be used.

Depending upon the time and temperature used in the heating step, the encapsulating surface film produced by this step will range from gel-like to rigid in character. Following this step the resulting composition is filtered to remove all extraneous matter and any microencapsulated particles that exceed 1 micron in size in any dimension. The finished product of this invention can consist of particles with a single degree of surface film hardness or, alternatively, can consist of particles of mixed surface film hardnesses. The desired quantity of said particles can be added to any appropriate physiological fluid. As such it will then comprise a product suitable for intravenous administration as a red blood cell substitute (resuscitation fluid). If desired, the microencapsulated particles may be used in much the same manner as packed red blood cells. If desired, the product may be lyophilized or otherwise dried using conventional techniques. The dried composition may be reconstituted as needed using an appropriate physiological fluid either as a blood substitute or as a perfusion fluid.

This invention provides for several alternative methods of preparing an intravenous red blood cell substitute. One alternative consists of the following steps: prepare polymerized albumin by adding 1 ethyl-3-dimethyl-aminopropyl-carbodiimide (EDC) to a 10% solution of monomeric albumin in an amount sufficient to produce a concentration of 5.0% w/v EDC in the product. Process in a colloid mill and/or a micro-fluidizer for about 10 minutes. Next, store the product at about 4° C. for about 10 hours. Next, mix a 10% w/v solution of pyridoxilated polymerized hemoglobin in an amount sufficient to achieve a hemoglobin concentration of about 10% by weight of the surfactant-water composition and, if desired, add about 2 millimoles of NADPH into the product and process in a colloid mill and/or a microfluidizer for about 10 minutes; following this step, mix a solution of polymerized lecithin into the solution in an amount sufficient to provide a polymerized lecithin concentration of about 8% by weight of the solution and process again in a colloid mill and/or a microfluidizer for about 10 minutes. Next, adjust the pH of the product to that of whole blood using HCl or NaOH as necessary. Following this step, adjust the isotonicity using plasma electrolytes in such concentration as will give the product the isotonicity of whole human blood. Adjust the viscosity as the next step so that the viscosity approximates that of whole blood. At this stage of manufacture the product may be used as a red blood cell substitute (resuscitation fluid) provided that it is first filtered to remove all extraneous matter and all particles that exceed 1 micron in size in any dimension. It is preferred, however, that the filtered product be processed further using either a chemical process based on a non-toxic crosslinking agent, such as glutaraldehyde, or a physical processing step, such as heat. The heating step is preferred and consists of heating the preparation for about 2 minutes at a temperature that may range from about 50° C. to about 70° C. producing a film that can range from gel-like to rigid in character. Following this step, the resulting composition is filtered to remove all extraneous matter and any microencapsulated particles that exceed 1 micron in size in any dimension. The finished product of this invention can consist of particles with a minimal degree of surface film hardness or, alternatively, it can consist of particles of mixed surface film hardnesses. The desired quantity of said particles can be added to any appropriate physiological fluid. As such it will then comprise a product suitable for intravenous administration as a red blood cell substitute (resuscitation fluid). If desired, the microencapsulated particles may be used in much the same manner as packed red blood cells. If desired, the product may be lyophilized or otherwise dried and reconstituted with any appropriate physiological fluid.

In accordance with another important embodiment of the present invention, the coacervate-based, compositions of the present invention can be used as a perfusion fluid for preventing degeneration of an organ or tissue used for transplantation or replacement of the organ or tissue for a mammal. Preferably, when used as a perfusion fluid, a hemoglobin-containing active compound, e.g., hemoglobin, stroma-free hemoglobin, pyridoxilated polymerized hemoglobin and/or modified hemoglobin, is present in the coacervate composition in an amount of 0.5% to 30% by weight of the coacervate composition, preferably 1% to 20% by weight of the coacervate composition. The coacervate-based perfusion fluids of the present invention are useful with or without a hemoglobin component and can be used in ambient air or may be oxygenated for additional oxygen transfer to the tissue or organs. The coacervate-based perfusion fluid is capable of maintaining viability of tissue and organs for up to at least 15 days and sometimes up to 30 days whereas prior art perfusion fluids generally are capable of sustaining tissue viability for only about 8 to 10 hours.

Another alternative coacervate-based intravenous red blood cell substitute using the methods of this invention comprise the following steps:

Mix 10% w/v of stroma-free hemoglobin into a solution of polymerized lecithin of about 20% concentration. Process the product in a colloid mill and/or a microfluidizer for about 2 minutes. Mix ascorbic acid of at least 0.1 gm per 100 ml of solution and an amount equal to 10% w/v (100 units/cc. in the finished product) of polymerized albumin into the product and process the resulting product in a colloid mill and/or a microfluidizer for about 5 minutes. Next, store the product for about 10 hours at 4° C. Adjust the pH of the preparation after the period of storage to about 7.4 using HCl or NaOH as necessary. Following this step, add electrolytes present in human plasma in such amount as will give the product the isotonicity of whole human blood. Next, adjust the viscosity of the product so that it approximates the viscosity of whole human blood. On completion of this step, the product comprises a microemulsion that consists of microencapsulated particles containing the hemoglobin component. At this stage of manufacture the product may be used as a red blood cell substitute (resuscitation fluid) provided that it is first filtered to remove all extraneous matter and all particles that exceed 1 micron in size in any dimension. It is preferred, however, that the filtered product be heated for about 2 minutes at about 70° C. The product then is filtered to remove all extraneous matter and all microencapsulated particles which exceed 1 micron in any single dimension. After this step, the product may be used as an intravenous blood substitute or stored preferably at 4° C. until needed.

While the processes described above use hemoglobin as the active component and yield intravenous venous red blood cell substitutes, this invention, as noted previously, enables the use of any medically useful composition as the active component to prepare compositions that can be administered via parenteral, oral, transdermal, transmucosal and inhalation routes.

Also, while the size of the particles of the injectable or parenteral red blood cell substitute should be 1 micron or less in size in any diameter, there are other embodiments of this invention in which the particle size comprising the composition can be more than 1 micron and further, in specific instances of this invention desirable compositions will be comprised of a combination(s) of particles with differing sizes; i.e., a given percentage of the particles will be 1 micron or less in size and the remaining percentage of particles will be 2 microns or more. Percentages and particle sizes will vary depending upon the specific formulation and the specific drug or combination of drugs used in the formulation.

In the preferred embodiment of an orally administered composition of this invention, the following process is used.

More specifically, warm a mixture of 7.5 gms of monoglyceride and 7.5 gms of diglyceride at from 65°–70° C. until a clear solution of the mixture is produced.

Unequal proportions of these glycerides may be used, but are not preferred. Equal or unequal proportions of mono-, di- and triglycerides also may be used. However, this mixture is also not preferred. When the warming step is completed the pharmaceutical component is mixed into the solution. The product of this step is subjected to a spray drying step while the product is gradually cooled. The product resulting from this step will be a powder comprising particles containing the pharmaceutical component.

The next step is designed to coat the particles with a coacervate film. The procedure is as follows. Make a suspension of the powder referred to above in 100 mls of water containing 10 gms of polymerized albumin and 10 gms of monomeric lecithin. Stir the composition for about two minutes. Add an appropriate alcohol dropwise, n-butyl alcohol is preferred, until a coacervate forms and coats the particles with a coacervate film, stirring during the addition of alcohol and afterward to insure that coacervate encapsulation of the particles continues for from ½ to 3 hours. The product then is stored for from 12 to 24 hours at about 4° C. The composition can be further microfluidized after encapsulation to further reduce the particle size, regardless of the number of films applied over the particles.

Following the storage step, the particles are separated from its liquid vehicle by filtration or other known appropriate methods and dried using any of the conventional drying techniques. This method yields a finished oral medically useful product comprised of a coacervate encapsulated pharmaceutically-active component.

If desired, the product referred to above can be processed further to produce a sustained release composition. This may be accomplished by any of several methods including application of heat, use of a cross-linking agent, such as glutaraldehyde, or covering the encapsulated product with one or more additional layers of coacervate film. The additional layer(s) of coacervate film is preferred. The additional layers can contain the same or different physiologically-active compound in a concentration of about 0.5% to about 50% based on the weight of the film, or may contain no additional physiologically-active component.

The procedure is as follows. Make a suspension of the powder referred to above in 100 mls of water containing 10 gms of polymerized albumin and 10 gms of monomeric lecithin. Stir the composition for about 2 minutes. Add n-butyl alcohol dropwise until a coacervate forms and coats the particles with a coacervate film, stirring during the addition of alcohol and afterward to insure that coacervate-encapsulation of the particles continues for from ½ to 3 hours. The product is then stored for from 12 to 24 hours at about 4° C.

Following the storage step, the particles are separated from their liquid vehicle by filtration, sieve or other known appropriate methods and washed and dried following any of the conventional drying techniques. Repeating this procedure will add an additional coacervate layer (film) containing no additional physiologically-active compound to the composition. The additional layers (films) can include one or more pharmaceutically-active component together with the coacervate-based encapsulating film if added to the coacervate composition, or may contain no additional physiologically-active component, as desired. This process may be repeated as often as required to produce one or more additional layers (films) with corresponding sustained release effects and/or containing any combination of active components. The particular active ingredient(s) and quantities of the active ingredient(s) within each layer can be varied to meet dosage requirements.

If desired, the structure of the surface of any of the layers referred to above can be hardened by applying heat to the product at a temperature and duration that will not adversely effect the activity of the pharmaceutic component. Any non toxic denaturing or polymerizing agent can be used in place of heat. If the heating step is incorporated in the described method, the release of the active component will be extended over a greater time period. It should be noted that in preparing the sustained release products of this invention, any single procedure or combination of procedures may be used provided that such procedure does not compromise the activity of the pharmaceutical component.

The particle size of the oral form of the composition of this invention can be any size suitable for the optimal delivery of the incorporated pharmaceutical component(s). The herein described oral formulation can be used in any of the known dosage forms such as tablets, capsules, syrups, caplets, powders, and the like.

An alternative formulation for an orally administered medical composition uses the following method. In this method, any non polar volatile, organic solvent may be used. In this instance carbon tetrachloride is the solvent. However, it must be emphasized that in the use of such solvents, all traces of this component must be removed in one of the manufacturing steps before proceeding to produce the finished product. The process is as follows: mix 10 gms of lecithin in 10cc of carbon tetrachloride; this will result in a clear solution. And the pharmaceutical component into the solution (e.g., 5 gms of erythromycin) and mix thoroughly. Using any appropriate method, i.e., spray drying, distillation or the like, process the product to remove the carbon tetrachloride. Spray drying is preferred. This process will yield powder-like particles comprised of lecithin and the pharmaceutical component encased in the lecithin matrix.

The next step is designed to coat the particles with a coacervate film. The procedure is as follows. Make a suspension of the powder referred to above in 100 mls of water containing 10 gms of polymerized albumin and 10 gms of monomeric lecithin. Stir the composition for about two minutes. Add an appropriate alcohol dropwise, n-butyl alcohol is preferred until a coacervate forms and coats the particles with a coacervate film, stirring during the addition of alcohol and afterward to insure that coacervate encapsulation of the particles continues for from ½ to 3 hours. If desired, the same or a different pharmacologically-active component can be added to the albumin-lecithin solution for incorporation into each additional film layer. The product then is stored for from 12 to 24 hours at about 4° C.

Following the storage step, the particles are separated from its liquid vehicle by filtration or other appropriate means and dried using any conventional method. This yields a finished oral product of the pharmaceutically-active component coated with a coacervate-based film. The product can be used to prepare capsules or reconstituted with an appropriate liquid(s), e.g., syrup, to produce a product with the desired clinical dose.

If desired, the product referred to above can be processed further to produce a sustained release composition. This may be accomplished by any of several methods including application of heat. Use of a cross-linking agent such as glutaraldehyde, or covering the encapsulated product with one or more additional layers of coacervate film. The additional layer of film is preferred, and any of the additional layers can be hardened for sustained release. It is preferred that the final layer not be hardened for prompt release of any active component contained therein.

The procedure is as follows. Make a suspension of the powder referred to above in 100 mls of water containing 10 gms of polymerized albumin and 10 gms of monomeric lecithin with or without 0.5% to 50% w/v of any physiologically-active compound. Stir the composition for about 2 minutes. And n-butyl alcohol dropwise until a coacervate forms and coats the particles with a coacervate film, stirring during the addition of alcohol and afterward to insure that coacervate-encapsulation of the particles continues for from ½ to 3 hours. The product is then stored for from 12 to 24 hours at about 4° C. Longer contact of the particles with the coacervate, while stirring, provides thicker films for control of film thickness and control of the amount of the active compound, if any, contained therein.

Following the storage step, the particles are separated from the liquid vehicle by filtration, sieve or other known appropriate methods and dried using any of the conventional drying techniques. This procedure will add a coacervate layer (film) to the composition; said layer (film) comprising the pharmaceutically-active component, if any, and the coacervate-based encapsulating film. This process may be repeated as often as required to produce one or more additional layers (films) with corresponding sustained release effects. The quantities of the active ingredient(s) within each layer can be varied to meet dosage requirements.

If desired, the structure of the surface of any of the layers referred to above can be hardened by applying heat to the product at a temperature and duration that will not adversely effect the activity of the pharmaceutic component. Any non toxic denaturing or polymerizing agent can be used in place of heat. If the heating step is incorporated in the described method, the release of the active component will be extended over a greater time period. It should be noted that in preparing the sustained release products of this invention, any single procedure or combination of procedures may be used provided that such procedure does not compromise the activity of the pharmaceutical component.

The particle size of the oral form of this alternative can be any size suitable for the optimal delivery of the incorporated pharmaceutical component(s). The herein described oral formulation can be used in any of the known dosage forms such as tablets, capsules, syrups, caplets, powders, and the like.

It is preferred that both the matrix containing the physiologically-active component(s) and the film that encapsulates it be coacervate derived or based. However, if desired, the matrix and/or film may be comprised of a non-coacervate composition. For example, the film may be comprised of such materials as glycerides, carnauba wax or sugar, and the like. If a sugar coating is to encapsulate the matrix, the particles comprised principally of matrix containing the active compound are dispersed in thick sugar syrup and the composition is mixed rigorously for from 30 seconds to 5 minutes or more depending on the desired film thickness. Following this step, the particles are separated from the vehicle by filtering if a consistent size particle is desired or centrifuged or by any other acceptable conventional process. If a non-coacervate based matrix is desired, the following method is used (See method for inhalation composition.) The film in such case will be coacervate based.

As noted previously, this invention provides for modifications of the basic formulation. Such modifications produce medically useful compositions which can be used either transdermally or transmucosally. These formulations involve processing the preferred oral composition to produce a gel.

When applied transmucosally, (i.e., intanasally or rectally), the gel composition of this invention adsorbs onto the mucous or rectal membranes and is absorbed therein through the mucosal tissue to the blood stream. The active component is released from the gel and is absorbed by the membranes, passing into the blood stream by way of the capillaries. The gel composition can be prepared in forms that provide for immediate release, sustained release or any combination thereof. The quantity of drug incorporated can be varied according to medical requirements. Only those active components which are intrinsically irritating to the nasal or rectal membranes are not desirable for incorporation in the gel.

Preparation of the gel can be accomplished, as an example, by mixing additional albumin, or pectin or combinations thereof into the oral formulations. Accordingly, hydrocolloids, particularly bioadhesive hydrocolloids, such as albumin and pectin, are added after the oral formulation has been completed to formulate the gel.

The gel composition can incorporate non polar drugs. These may be further subclassified as drugs or other physiologically-active compound(s) which are heat sensitive and drugs or other physiologically-active compound(s) which are heat stable. Thus, erythromycin is an example of a heat stable composition; insulin is regarded as a heat sensitive composition. In the process of this invention, heat stable drug preparations can be "fixed", i.e., the encapsulating film can be hardened or structured in the manner described. On the other hand, heat sensitive drug preparations can be structured by the application of physical techniques such as radiation or physicochemical means, such as n-butyl alcohol which form a coacervate and then an encapsulating film of the composition.

The process to prepare the gel is based on any of the oral preparations described above. It is preferred however, to use the above-described example method incorporating the mono and di glyceride components. More specifically, warm a mixture of 7.5 gms of monoglyceride and 7.5 gms of diglyceride until a clear solution of the mixture is produced.

Unequal proportions of these glycerides may be used, but are not preferred. Equal or unequal proportions of mono-, di- and triglycerides also may be used. However, this mixture is also not preferred. When the warming step is completed the pharmaceutical component is mixed into the solution. The solution then is subjected to a spray drying step while the product is gradually cooled. The product resulting from this step will be a powder comprising particles containing the pharmaceutical component.

The next step is designed to coat the particles with a coacervate film. The procedure is as follows. Make a suspension of the powder referred to above in 100 mls of water containing 10 gms of polymerized albumin and 10 gms of monomeric lecithin. Stir the composition for about two minutes. Add an appropriate alcohol dropwise, n-butyl alcohol is preferred, until a coacervate forms and coats the particles with a coacervate film, stirring during the addition of alcohol and afterward to insure that coacervate encapsulation of the particles continues for from ½ to 3 hours. The product is then stored for from 12 to 24 hours at about 4° C.

Following this step, the composition is processed through centrifugation, sieving or other appropriate separatory techniques to separate the coacervate drug particles from its vehicle and to retain particles having a gel-like surface. Following this step, a bioadhesive hydrocolloid, such as albumin or pectin or any appropriate combination thereof, is mixed into the composition. The quantity of albumin that may be used ranges from about 2% w/v to about 20% w/v; the range of pectin that may be used also ranges from about 2% w/v to about 20% w/v. 10% w/v of pectin is preferred. The pH of the preparation is adjusted to about 7.4 by the addition of HCl or NaOH, as required.

In the case of heat unstable drugs, and the like, the process described above is modified. Following the coating step the composition is stored at room temperature for about 24 to 72 hours. After this period, the composition may be used or the composition may be heated at from 40° to 50° C. until the particles assume a soft gel-like character. It is preferred that following the coating steps the preparation can be processed by the dropwise addition of a suitable protein denaturing agent, such as ethyl alcohol, n-butyl alcohol, isopropyl alcohol, and the like, until the structure of the interfaces of the particles range from soft gel-like to semi-solid. N-butyl alcohol is preferred.

If desired, a sustained release effect for this composition is achieved by subjecting portions of the product to heat, a cross-linking agent or radiation or combinations thereof. Heat is preferred. The following procedure is provided as an example. 20% of the composition is not heat treated. 20% is heated at 70° C. for 40 seconds; 20% is heated at 65° C. for 60 seconds and the remaining 20% is heated at 60° C. for 90 seconds. The point to be made is that the exact combination of heat and time depends upon the specific drug being used and the desired schedule of drug release.

Microparticles comprising the transmucosal products can range from less than 1 micron to 6 microns or more in size. Particles less than 1 micron in size are preferred. The quantity of drug or other active agent to be incorporated into the composition is determined by medical considerations and can range from ½ of the convention oral or intravenous does to four times the conventional dose.

After the composition is produced, e.g., normal or sustained release or combinations of normal and sustained release, the composition is placed in any dosage form suitable for nasal or rectal administration.

The process used to produce the transmucosal gel is used to produce the transdermal gel except that the adjustment of the pH is not required. In this embodiment, the drug or combination of drugs is sequestered or otherwise incorporated in a coacervate-based composition comprised of microencapsulated particles which range from semi-liquid to gel-like in structure. The composition(s) may be applied directly to the skin in such forms as ointments or gels and incorporated in a cellulose based patch or a suitable container. In the preferred mode, the composition is placed in a container and used in conjunction with an appropriate sonifier. By this technology an unexpected degree of drug absorption by the skin is achieved. Moreover, the transdermal gel and sonifier permits any scheduled administration or emergency administration as required.

While transdermal methods of drug administration are known, the literature does not reveal a technique in which a coacervate-based microencapsulated composition is used in conjunction with a sonifier. In this embodiment of the invention, use of a sonifier produces a local cavitational effect in the skin and in underlying tissue fluids, the net effect of which is to make the skin more permeable to the drug(s) being administered and to make the drug more available to the underlying tissues, including the capillaries and microcirculation. The cavitational effect is induced when sonification is applied and is ended when sonification is terminated. The application of the sonifier permits intermittent increases in skin permeability to administered drugs as required.

In the preferred practice of this invention, the finished product, e.g., the coacervate-based gel containing the medication required for either single or multiple doses, is placed in a suitable, leak proof container approximately the size of a wrist watch. The bottom of the container should be made of a semiporous or microporous support layer, e.g., a cellulose layer. The sides and top of the container should be made of plastic or other suitable non toxic material. The top of the container should have an opening large enough to contain the head of a hand held sonifier such as NOVOPHON (manufacturer: Elredge Resources). Any suitable sonifier presently used for physical therapy can be used in accordance with this embodiment of the present invention. The container should be constructed such that a thin layer of either aluminum foil or plastic or other composition suitable to transmit the sonifier effects to the medication and the skin is placed between the medication and the sonifier head. The medication is administered transdermally, as required by placing the head of the sonifier in the container and activating the sonifier for the time necessary to administer the prescribed dose of medication.

Presently available transdermal patches are characterized by a continuous straight line release of the drug. This has been shown to be problematic with drugs such as nitroglycerin. In addition, such release is inconsistent with the body's normal release of hormones, enzymes and the like. Thus, by way of illustration, the body normally secretes very small quantities of insulin throughout the day. Upon ingestion of food, however, a surge of insulin is released. This invention permits a virtual duplication of such release phenomena not only for endogenous compositions but for medically useful exogenous compounds as well. In addition, this invention enables transdermal administration of medication according to any medically prescribed schedule.

This invention differs importantly from Zeffarone (U.S. Pat. No. 4,557,723) in that in his techniques a rate controlling membrane is used and is limited to drugs which show natural diffusive flux. No such features and limitations are present in this embodiment of the present invention. Ariura (U.S. Pat. No. 4,474,570) uses iontophoresis as the driving force. However, the Ariura device produces an unacceptable degree of heat in its operation. The present invention does not generate unacceptable heat; its driving force not only differs but its effect upon the skin differs from that of iontophoresis. The Sibalis U.S. Pat. No. 4,557,723 describes an electrophoretic technology but also identifies the problems with known transdermal delivery devices. The Sibalis technology is fundamentally unrelated to the transdermal-sonifier embodiment of the present invention. Sibalis relies upon battery supplied electrical current which battery must be changed according to different flow requirements. Sibalis simply refers to a medicament. In the Ecanow patent, medications are encapsulated in coacervate-based films. The herein described use of localized sound waves as opposed to electrical current is an unobvious modification in that in the herein disclosed use, sound waves produce an effect on the skin and tissue fluids of the site that renders the site more permeable to drugs within the coacervate compositions. Sibalis and others who have described transdermal inventions do not disclose such properties.

Embodiments of the disclosed transdermal composition may be comprised of a matrix of hydrated hydrophilic colloids of which coacervate compositions comprise one class of such colloids. Gels constitute another class. Other compositions that could be used to provide the substrate for the medicament in this invention include any gelled silicon media, petrolatum and the like. In this invention, a gel based upon any acceptable coacervate formulation is preferred. Any of the described formulations which eventuate as oral or parenteral products of this disclosure can constitute the basis for preparing the transdermal product. Medications that can be incorporated in the gel for transdermal administration include enzymes, biologicals, drugs and other useful medicaments. In short, any medically useful molecule capable of penetrating the skin may be used in this invention. Use of the sonifier in conjunction with this composition acts in an unexpected manner to increase the rate of transdermal passage.

The method to produce a coacervate-based inhalant composition, as another embodiment of the present invention for administration of any suitable medication is as follows:

A method to prepare an inhalant medication is as follows:

Heat a mixture of about 7.5 gms of monoglyceride and about 7.5 gms of diglyceride at a temperature of from 70° to 75° C. until a clear solution of the mixture is produced. Mix the desired amount of the pharmaceutical component into the solution. Next, process the product by means of a spray drying step to produce a powder form of the product. Next, make a suspension of the powder in 100 mls of water containing 10 gms of polymerized albumin and 10 gms of monomeric lecithin. Stir the composition for about two minutes. Add an appropriate alcohol dropwise, n-butyl alcohol is preferred. During the addition of alcohol the product should be stirred gently until a coacervate forms and coats the particles with a coacervate film, to insure that coacervate encapsulation of the particles continues for from ½ to 3 hours. After this step, adjust the pH to about 7.4 and if desired, and store for from 12 to 24 hours at about 4° C.

Following the storage step, the particles are separated from the liquid vehicle by filtration or other appropriate means. The particles are processed using a colloid mill and/or a microfluidizer and sieving or other filtering procedures to produce particles which are 1 micron or less in size. After this step, the quantity of particles necessary to produce the required dose is mixed into any appropriate fluid, such as the liquid vehicle separated from the particles. The product comprises an inhalant medication and is administered by nebulizer or other mist spraying apparatus.

The examples which follow are representative embodiments. They do not constitute the entire range of medications that can be used in this invention.

EXAMPLE 1

To 100 mls of a 10% w/v solution of polymerized albumin add 10 gms of stroma-free hemoglobin from any appropriate source. Next, add about 2 millimoles of glutathione and 8 gms of monomeric lecithin to the composition. Using a colloid mill and/or a microfluidizer, process the product for approximately 2 minutes. During this processing step add 10% of 1 ethyl-3 dimethyl aminopropyl carbodiimide (EDC). Following this processing step store the composition for 12 hours at 4° C. The pH of the composition then is adjusted through the use of HCl or NaOH to approximate the pH of normal whole blood. This adjustment is made prior to the step of colloid mill and/or a microfluidizer processing and after the period of storage. Isotonicity also is adjusted by adding plasma electrolytes in such concentration as will approximate the isotonicity of whole human blood. This step is taken following the period of storage. Adjustment of viscosity to approximate that of whole human blood is made after the period of storage. At this point, the product may be used as a red blood cell substitute, provided that it is filtered to eliminate all extraneous matter and all particles larger than 1 micron in size. It is preferred that the product be processed further using a heating step designed to harden the coacervate-based film that envelopes the particle(s) containing the hemoglobin component. In the heating step, the composition is heated for 2 minutes at 70° C. Following this step the composition is filtered to eliminate all extraneous matter and all particles larger than 1 micron in size. Particles of 1 micron or less then can be put into an appropriate physiological fluid and transfused or stored at 4° C. and reconstituted as a red blood cell substitute (resuscitation fluid) using an appropriate physiological fluid.

EXAMPLE 2

The procedure of Example 1 is followed except that polymerized lecithin is used in place of monomeric lecithin.

EXAMPLE 3

The procedure of Example 2 is followed except that monomeric albumin is used in place of polymerized albumin.

EXAMPLE 4

The procedure of Example 1 is followed but, in addition, the encapsulated microparticles are subjected to a lyophilizing process to produce a powder form of the composition that can be mixed into an appropriate physiologic fluid as needed to produce a red blood cell substitute.

EXAMPLE 5

The procedure of Example 1 is followed except that 10% w/v of modified hemoglobin is used in place of stroma-free hemoglobin and about 0.1% urea is added.

EXAMPLE 6

The procedure of Example 1 is followed except that the heating step consists of heating the composition at 50° C. for 1 minute.

EXAMPLE 7

The procedure of Example 1 is followed except that stroma-free hemoglobin encapsulated in liposomes comprises the hemoglobin component.

EXAMPLE 8

Heat a mixture of about 7.5 gms of monoglycerize and about 7.5 gms of diglyceride at a temperature of from 70° to 75° C. until a clear solution of the mixture is produced. Mix 15 gms of erythromycin into the glyceride solution thoroughly. The objective of the next step is to convert the composition to a powder form. This may be accomplished by any conventional form such as spray drying. In this instance the warm product comprised of the glyceride components and the erythromycin is gradually cooled to give a powder. The particle size of the product following the spray drying will range from about 2 microns to 500 microns. The finished product may consist of a single size or combination of sizes.

The next step is designed to coat the particles with a coacervate film. The procedure is as follows. Make a suspension of the powder referred to above in 100 mls of water containing 10 gms of polymerized albumin and 10 gms of monomeric lecithin. Stir the composition for about two minutes. Add an appropriate alcohol dropwise, n-butyl alcohol is preferred, until a coacervate forms and coats the particles with a coacervate film, stirring during the addition of alcohol and afterward to insure that coacervate encapsulation of the particles continues for from ½ to 3 hours. The product is then stored for from 12 to 24 hours at about 4° C.

Following the storage step, the particles are separated from the liquid vehicle by filtration or other appropriate means and dried using any conventional method. This yields a finished oral product of a coacervate coated pharmaceutically-active component, coated with the coacervate-based film. The product can be used to prepare capsules or reconstituted with an appropriate liquid(s), e.g., syrup, to produce a product with the desired clinical dose.

EXAMPLE 9

The procedure of Example 8 is followed, but in addition, the encapsulated microparticles are subjected to a lyophilizing process before prepared as capsules, tablets, or liquid preparations.

EXAMPLE 10

The process of Example 9 is followed except the product is divided into four portions. Portion 1 is heated at 50° C. for 2 minutes; portion 2 is heated at 60° C. for 2 minutes; portion 3 is heated at 65° C. for 2 minutes; portion 4 is heated at 70° C. for 1½ minutes. After the heating step, the products are combined thereby forming a sustained release composition.

EXAMPLE 11

The process of Example 9 is followed except that the finished product of Example 9 is processed further by adding an additional coacervate (film) coat to the product as per the process of Example 9. The resulting composition comprises a sustained release composition with two release rates.

EXAMPLE 12

The process of Example 11 is followed except that 20% of the finished product is processed to receive an additional coacervate (film) coat, two additional coats (films) are applied to 30% of the product, and 50% of the product comprises the original finished product of Example 11. The products are mixed together thereby comprising a composition with sustained release characteristics, i.e., three release rates.

EXAMPLE 13

The procedure of Example 8 is followed except that regular insulin is used in place of erythromycin and in a quantity that will yield a finished oral composition containing 40 units of insulin per dose.

EXAMPLE 14

The procedure of Example 13 is followed except that regular insulin incorporated in liposomes is used in as the active component.

EXAMPLE 15

The procedure of Example 8 is followed, except that urokinase in an amount that will give unit dose of 50,000 IU is used in place of erythromycin and the encapsulated microparticles are subjected to a lyophilizing process to produce a powder which can be placed in capsules for oral use or used to reconstitute a liquid dosage form by using an appropriate liquid.

EXAMPLE 16

The procedure of Example 8 is followed except that 15 gms of erythromycin encapsulated in liposomes is used.

EXAMPLE 17

The procedure of Example 8 is followed except that lidocaine is used in place of erythromycin and in a quantity that will yield a finished composition containing 1% lidocaine/5 ml per unit dose.

EXAMPLE 18

The procedure of Example 8 is followed except that 500 mgs of fluorouracil encapsulated in liposomes is used as the active component.

EXAMPLE 19

The procedure of Example 11 is followed except that following the application of the additional coacervate coating to the product the composition then is heated at 70° C. for 60 seconds.

EXAMPLE 20

The procedure of Example 8 is followed except that erythromycin is replaced with urokinase in an amount that will yield 50,000 IU of urokinase per unit dose.

EXAMPLE 21

The procedure of Example 20 is followed except that the urokinase component is encapsulated in liposomes.

EXAMPLE 22

This process consists of the following steps: prepare polymerized albumin by adding 1 ethyl-3-di-methyl-aminopropyl-carbodiimide to a 10% solution of monomeric albumin in an amount sufficient to produce a concentration of 5.0% w/v EDC in the product. Process in a colloid mill and/or a microfluidizer for about 2 minutes. Next, store the product at about 4° C. for about 10 hours. Mix into the product a solution of stroma-free hemoglobin to a concentration of about 10% by weight of the composition and about 2 millimoles of NADPH into the product and process in a colloid mill and/or a microfluidizer for about 5 minutes; following this step, mix into the solution polymerized lecithin in an amount sufficient to provide the solution with a concentration of polymerized lecithin of about 8% by weight into the product, and process again in a colloid mill and/or a microfluidizer for about 3 to 5 minutes. Next, adjust the pH of the product to that of whole blood using HCl or NaOH as necessary. Following this step, adjust the isotonicity using plasma electrolytes in such concentration as will give the product the isotonicity of whole human blood. Adjust the viscosity as the next step so that the viscosity approximates that of whole blood. At this stage of manufacture the product may be used as a red blood cell substitute (resuscitation fluid) provided that it is first filtered to remove all extraneous matter and all particles that exceed 1 micron in size in any dimension. It is preferred, however, that the filtered product be processed further using either a chemical process based on a non-toxic crosslinking agent, such as glutaraldehyde, or a physical processing step, such as heat. The heating step is preferred and consists of heating the preparation for about 2 minutes at a temperature that may range from about 50° C. to about 70° C. producing a film that can range from gel-like to rigid in character. Following this step, the resulting composition is filtered to remove all extraneous matter and any microencapsulated particles that exceed 1 micron in size in any dimension. The finished product of this invention can consist of particles of 1 micron or less in size with a minimal degree of surface film hardness or, alternatively, it can consist of particles of mixed surface film hardnesses. The desired quantity of the particles can be added to any appropriate physiological fluid. As such, it will then comprise a product suitable for intravenous administration as a red blood cell substitute (resuscitation fluid). If desired, the microencapsulated particles may be used in much the same manner as packed red blood cells. If desired, the product may be lyophilized or otherwise dried and reconstituted as a resuscitation fluid with any appropriate physiological fluid.

EXAMPLE 23

The procedure of Example 22 is followed except that polymerized lecithin is used in place of monomeric lecithin.

EXAMPLE 24

The procedure of Example 22 is followed except that stroma-free hemoglobin incorporated in liposomes is used in place of stroma-free hemoglobin.

EXAMPLE 25

The procedure of Example 22 is followed but in addition, the encapsulated microparticles are subjected to a lyophilizing process to produce a powder form of the composition that can be mixed into an appropriate physiological fluid to produce a red blood cell substitute.

EXAMPLE 26

The procedure of Example 22 is followed except that 10% w/v of modified hemoglobin is used in place of stroma-free hemoglobin.

EXAMPLE 27

The procedure of Example 22 is followed except that the heating step consists of heating the composition at 50° C. for 2 minutes.

EXAMPLE 28

The procedure of Example 8 is followed, except that erythromycin is replaced with heparin in an amount that will give 1000 USP units/ml in the finished product; the composition is subjected to a lyphilizing process to produce a powder form of the composition which can be prepared as tablets or capsules or reconstituted using any appropriate pharmaceutical fluid thereby comprising a useful oral medication.

EXAMPLE 29

The procedure of Example 1 is followed except that (1) 5 gms of erythromycin replaces the hemoglobin and (2) the steps involving glutathione and the addition of 1-ethyl-3 dimethyl aminopropyl-carbodiimide are omitted. The step to adjust the pH of the composition to approximately 7.4 is made after the storage period. After the heating and filtering steps, the microparticles are dispersed in any appropriate physiological fluid. The product then is ready for parenteral administration or stored, preferably under refrigeration, until needed.

EXAMPLE 30

The procedure of Example 29 is followed except that urokinase is used in place of erythromycin in a quantity that will yield a finished composition containing 50,000 IU of urokinase per unit dose.

EXAMPLE 31

The procedure of Example 29 is followed except that 500 mgs of fluorouracil is substituted for erythromycin and the sizes of the microparticles of the finished product range from less than 1 micron to 4 microns.

EXAMPLE 32

The procedure of Example 1 is followed except that 10% w/v of erythropoietin is used in place of hemoglobin, and the steps involving the use of glutathione and 1 ethyl-3-dimethyl aminopropyl carbodiimide are omitted. The finished product comprises a useful intravenous composition of erythropoietin. The product can be lyophilized to produce a powder form of the composition and stored under refrigeration or reconstituted with an appropriate physiological fluid for intravenous administration.

EXAMPLE 33

The procedure of Example 22 is followed except that 10% w/v of modified hemoglobin is used in place of stroma-free hemoglobin.

EXAMPLE 34

The procedure of Example 31 is followed except that the fluorouracil is encapsulated in microparticles of 2 to 4 microns in size. This product is combined with the erythromycin product of Example 29; the mixture comprising an intravenous composition composed of two active components with differing particle sizes, eryrhtomycin 1 micron or less; fluorouracil 2-4 microns.

EXAMPLE 35

The procedure of Example 22 is followed, except that the stroma-free hemoglobin encapsulated in liposomes is used as the starting hemoglobin component.

EXAMPLE 36

The procedure of Example 22 is followed but, in addition, the encapsulated microparticles are subjected to a lyophilizing process to produce a powder form of the composition that can be stored at 4° C. or reconstituted with an appropriate physiologic fluid to produce a red blood cell substitute (intravenous).

EXAMPLE 37

The procedure of Example 31 is followed except that the erythromycin and fluorouracil incorporated in liposomes are used as the active components.

EXAMPLE 38

The procedure of Example 22 is followed except that 275 mgs of erythromycin is used in place of the hemoglobin component and the steps involving the use of NADPH and 1 ethyl-3-dimethyl-aminopropyl carbodiimide are omitted. The step in which the pH is adjusted to approximately 7.4. is made after the storage period. After the heating and filtering steps, the microparticles are dispersed in any appropriate physiological fluid. The product is then ready for intravenous administration or it may be stored, preferably at 4° C.

EXAMPLE 39

The procedure of Example 38 is followed except that leuprolide in a quantity that will yield leuprolide mg/0.2 ml in the finished product is substituted for erythromycin.

EXAMPLE 40

The procedure of Example 39 is followed, except that urokinase in that quantity as will give 50,000 IU activity per dose in the finished product is used in place of leuprolide and the product is lyophilized. The product can be reconstituted with an appropriate physiological fluid for intravenous

EXAMPLE 41

The procedure of Example 40 is followed except that 60,000 IU of urokinase incorporated in liposomes, is used as the active component.

EXAMPLE 42

The procedure of Example 40 is followed except that 500 mgs of fluorouracil replaces urokinase and is processed so that the particle size of the particles ranges from 2-4 microns and the product of Example 38 is mixed with the product of this Example. This comprises an Example of a combination of two compositions, each with a different particle size.

EXAMPLE 43

Mix to a concentration of 10% w/v stroma-free hemoglobin into a solution of polymerized lecithin of about 20% concentration. Process the product in a colloid mill and/or a microfluidizer for about 2-3 minutes. Mix ascorbic acid of at least 0.1 gm per 100 ml of solution and an amount equal to 10% w/v (100 units/cc. in the finished product) of polymerized albumin into the product and process the resulting product in a colloid mill and/or a microfluidizer for about 5-7 minutes. Next, store the product for about 10 hours at 4° C. Adjust the pH of the preparation after the period of storage to about 7.4 using HCl or NaOH as necessary. Following this step, add electrolytes present in human plasma in such amount as will give the product the isotonicity of whole human blood. Next, adjust the viscosity of the product so that it approximates the viscosity of whole human blood. On completion of this step, the product comprises a microemulsion that consists of microencapsulated particles containing the hemoglobin component. At this stage of manufacture the product may be used as a red blood cell substitute (resuscitation fluid) provided that it is first filtered to remove all extraneous matter and all particles that exceed 1 micron in size in any dimension. It is preferred, however, that the filtered product be heated for about 2 minutes at about 70° C. The product then is filtered to remove all extraneous matter and all microencapsulated particles which exceed 1 micron in any single dimension. After this step, the product may be used as an intravenous blood substitute or stored, preferably at 4° C., until needed.

EXAMPLE 44

The procedure of Example 43 is followed except that stroma-free hemoglobin incorporated in liposomes is used in place of stroma-free hemoglobin.

EXAMPLE 45

The procedure of Example 43 is followed but in addition, the encapsulated microparticles are subjected to a lyophilizing process to produce a powder form of the composition that can be mixed into an appropriate physiological fluid to produce a red blood cell substitute.

EXAMPLE 46

The procedure of Example 43 is followed except that 10% w/v of modified hemoglobin is used in place of stroma-free hemoglobin.

EXAMPLE 47

The procedure of Example 43 is followed except that the heating step consists of heating the composition at 50° C. for about 2 minutes.

EXAMPLE 48

The procedure of Example 43 is followed except that (1) 275 mgs of erythromycin replaces the hemoglobin component. The step in which the pH is adjusted to approximately 7.4. is made after the storage period. After the heating and filtering steps, the resulting microparticles are dispersed in any appropriate physiological fluid. The product then is ready for intravenous administration or storage at 4° C.

EXAMPLE 49

The procedure of Example 43 is followed, but in addition, the composition is lyophilized to produce a powder form of the product which can be reconstituted with any appropriate physiological fluid.

EXAMPLE 50

The procedure of Example 48 is followed, except that 500 mgs of fluorouracil is used in place of erythromycin and the sizes of the microparticles are in the range of 2 to 4 microns.

EXAMPLE 51

The procedure of Example 50 is followed except that the fluorouracil is encapsulated in liposomes before being encapsulated within the coacervate composition.

EXAMPLE 52

The procedure of Example 48 is followed except that leuprolide in a quantity that will yield leuprolide 10 mg/0.2 ml in the finished product is substituted for erythromycin.

EXAMPLE 53

The procedure of Example 8 is followed except that 200 mgs. of ibuprofen is used in place of erythromycin.

EXAMPLE 54

The procedure of Example 43 is followed except that 10% w/v of erythropoietin is used in place of hemoglobin and the step involving the use of ascorbic acid is omitted. The finished product comprises a useful intravenous composition of erythropoietin.

EXAMPLE 55

The product of Example 48 is mixed with the product of Example 50 to produce a combination of two compositions with differing particle sizes.

EXAMPLE 56

The procedure of Example 48 is followed except that leuprolide is used in place of erythromycin, and in an amount that will give 4 mgs/0.2 ml of leuprolide in the finished product.

EXAMPLE 57

The procedure of Example 48 is followed except that erythromycin is replaced with urokinase in an amount that will give 50,000 IU per dose in the finished product.

EXAMPLE 58

The procedure of Example 56 is followed, except that the leuprolide component is encapsulated in liposomes.

EXAMPLE 59

The procedure of Example 8 is followed except that after the addition of n-butyl alcohol and the stirring step, about 10% w/v of pectin is mixed into the product now comprised of the microparticles separated from the vehicle. After the step in which pectin is added, the pH of the composition is also adjusted using either HCl or NaOH as required to about 7.4. The product comprises a composition that can be administered transmucosally and/or transdermally.

EXAMPLE 60

The process of Example 59 is followed except that 5% nitroglycerin is used to replace erythromycin and 5% w/v of albumin is used in place of pectin. The finished product comprises a transmucosal medication.

EXAMPLE 61

The process of Example 59 is followed except that 5 mg/ml of lidocaine replaces the nitroglycerin.

EXAMPLE 62

The procedure of Example 59 is followed except that a heating step of about 50° C. for 40 seconds replaces the step using n-butyl alcohol. Following heating, the product is processed to separate the microparticles from the vehicle. About 10% w/v pectin is mixed into the resulting microparticle composition. During the step in which the pectin is added, the pH of the product is adjusted to about 7.4 using either HCl or NaOH as required.

EXAMPLE 63

The procedure of Example 59 is followed except that 5% nitroglycerin is used in place of erythromycin; storage of the composition at room temperature for about 24 hours replaces the heating step.

EXAMPLE 64

The procedure of Example 59 is followed except that 5% w/v albumin replaces pectin and 10% nitroglycerin is used.

EXAMPLE 65

The process of Example 59 is followed except that 5% nitroglycerin is used to replace erythromycin and 5% w/v of albumin is used in place of pectin. The finished product comprises a transmucosal medication.

EXAMPLE 66

The process of Example 65 is followed except that 5 mg/ml of lidocaine replaces the nitroglycerin.

EXAMPLE 67

The process of Example 66 is used except that 100 units of regular insulin is used instead of lidocaine.

EXAMPLE 68

The process of Example 59 is followed except that 0.1% ascorbic acid is added at the same time pectin is added.

EXAMPLE 69

The process of Example 62 is used except that 100 units of insulin is used instead of erythromycin.

EXAMPLE 70

The process of Example 62 is used except that 0.2% ascorbic acid is added when pectin is added.

EXAMPLE 71

The procedure of Example 62 is followed except that 40 units of insulin is used in place of erythromycin; storage of the composition at room temperature for about 24 hours replaces the heating step.

EXAMPLE 72

Mix about 10 gms of lecithin into about 10 cc of carbon tetrachloride. Add 5 gms of erythromycin to the solution. Spray dry the product until all traces of carbon tetrachloride are removed. The resulting product will be comprised of powder-like particles comprised of erythromycin and covered by a film of lecithin. Next, make a suspension of the powder in 100 mls of water containing 10 gms of polymerized albumin and 10 gms of monomeric lecithin. Stir the composition for about two minutes. Add an appropriate alcohol dropwise, n-butyl alcohol is preferred. During the addition of alcohol the product should be stirred gently until a coacervate forms and coats the particles with a coacervate film. Stirring continues for from ½ to 3 hours to insure coacervate encapsulation of the particles. After this step, adjust the pH to about 7.4 and if desired, store for from 12 to 24 hours at about 4° C.

Following the storage step, the particles are separated from the liquid vehicle by filtration or other appropriate means and dried using any conventional method. This yields a finished oral product comprised of coacervate coated erythromycin. The product can be used to prepare tablets, capsules or reconstituted with an appropriate liquid(s), e.g., syrup, to produce a product with the desired clinical dose.

EXAMPLE 73

Mix about 10 gms of lecithin into about 10 cc of carbon tetrachloride. Add 3 gms of erythromycin into the solution. Distill the product until all traces of the carbon tetrachloride are removed and the product, comprised of lecithin and erythromycin, is in the form of a viscous residue. Mix about 50 mls of a 10% solution of albumin into the product. Add 100 mls of distilled water and centrifuge the composition for about 10 minutes at about 2500 rpm. The particles now separated from their vehicle are collected. They comprise an oral erythromycin coated by a coacervate film.

EXAMPLE 74

The method of Example 73 is followed except that the steps that begin with the addition of the albumin component are repeated.

EXAMPLE 75

The process of Example 72 is followed except that the product of Example 72 is converted to a sustained release preparation using the following method. Make a suspension of the powder referred to above in 100 mls of water containing 10 gms of polymerized albumin and 10 gms of monomeric lecithin. Stir the composition for about two minutes. Add n-butyl alcohol dropwise until a coacervate forms and coats the particles with a coacervate film, stirring continues for from ½ to 3 hours during the addition of alcohol and afterward to insure coacervate encapsulation of the particles. The product is then stored for from 12 to 24 hours at about 4° C.

Following the storage step, the particles are separated from the liquid vehicle by filtration and dried. The resulting composition comprises a sustained release medication useful for oral administration.

EXAMPLE 76

The process of Example 74 is followed except that the product of Example 74 is converted to a sustained release preparation using the following method. Make a suspension of the powder referred to above in 100 mls of water containing 10 gms of polymerized albumin and 10 gms of monomeric lecithin. Stir the composition for about two minutes. Add n-butyl alcohol dropwise until a coacervate forms and coats the particles with a coacervate film, stirring continues for from ½ to 3 hours during the addition of alcohol and afterward to insure coacervate encapsulation of the particles. The product is then stored for from 12 to 24 hours at about 4° C.

Following the storage step, the particles are separated from its liquid vehicle by filtration and dried. The resulting composition comprises a sustained release medication useful for oral administration.

EXAMPLE 77

Mix about 6 gms of lecithin in about 200 mls of water; add about 24 mls of an appropriate alcohol such as n-butyl alcohol dropwise to the mixture. Next mix a solution comprised of about 3 gms of NaCl and about 60 mls of water into the lecithin-alcohol composition and allow to stand until a two phase coacervate is produced. Separate the two phases and add 20% acetylcysteine to the coacervate phase. Mix thoroughly. The pH is adjusted to about 8.0 after which the composition containing the medication may be administered by nebulizer which sprays a mist of the particles having a particle size of 1 micron or less.

EXAMPLE 78

The process of Example 77 is followed except that 5 gms of lecithin is added to the coacervate phase in place of acetylcysteine and the pH is adjusted to about 7.4 using HCl or HaOH as required.

EXAMPLE 79

The process of 77 is followed except that the lecithin-coacervate phase, per se, is adjusted to a pH of about 7.4 and used as an inhalant medication.

EXAMPLE 80

Heat a mixture of about 7.5 gms of monoglyceride and about 7.5 gms of diglyceride at a temperature of from 70 to 75° C. until a clear solution of the mixture is produced. Mix 15 gms of erythromycin into the glyceride solution thoroughly. Next, process the product by means of a spray drying step to produce a powder form of the product. Next, Make a suspension of the powder in 100 mls of water containing 10 gms of polymerized albumin and 10 gms of monomeric lecithin. Stir the composition for about two minutes. Add n-butyl alcohol dropwise until a coacervate forms and coats the particles with a coacervate film, stirring for from ½ to 3 hours during the addition of alcohol and afterward to insure coacervate encapsulation of the particles. The product is then stored for from 12 to 24 hours at about 4° C.

Following the storage step, the particles are separated from the liquid vehicle by filtration or other appropriate means. The particles are processed using a colloid mill and/or a microfluidizer and sieving procedures to produce particles which are 1 micron or less in size. After this step, the quantity of particles necessary to produce the required dose is mixed into any appropriate fluid including the liquid vehicle referred to above. The product comprises an inhalant medication and is administered by nebulizer or other mist spraying apparatus.

EXAMPLE 81

The method of Example 77 is followed except that 15 gms of erythromycin is used in place of acetylcysteine and the pH adjustment is made to about 7.4.

EXAMPLE 82

The procedure of Example 1 is followed except that (1) 275 mgs of erythromycin is dispersed in oleic acid of about 10% w/v as the first step of the process and the step using the reducing agent is omitted. The step to adjust the pH of the composition to approximately 7.4. is made after the storage period. After the heating and filtering steps, the microparticles are dispersed in any appropriate physiological fluid. The product is then ready for oral administration or stored, preferably under refrigeration, until needed. The composition may be administered orally, if desired.

EXAMPLE 83

The procedure of Example 82 is followed except that the object of the heating step in this method is to produce microparticles which are gel-like in character. The composition is heated at about 60° C. for about 45 seconds. The resulting composition then is centrifuged to separate the particles from the vehicle of the product; following this step, about 10% w/v of pectin and about 0.1% of ascorbic acid are mixed into the product now comprised of the microparticles separated from the vehicle. During the steps in which pectin and ascorbic acid are added, the pH of the composition is also adjusted using either HCl or NaOH as required to about 7.4. The product comprises a nasally or rectally administered medically useful composition. The addition of ascorbic acid can be omitted.

EXAMPLE 84

The procedure of Example 83 is followed except that in place of the heating step, the product is stored at room temperature for about 24 hours and 5% nitroglycerin is used in place of erythromycin.

EXAMPLE 85

The procedure of Example 84 is followed. The finished product however is applied to the skin. The drug is released from the composition and enters the circulation through the skin.

EXAMPLE 86

The procedure of Example 84 is followed except that 4000 mcg of vitamin B-12 is used in place of erythromycin.

EXAMPLE 87

The procedure of Example 84 is followed except that 4 mgs/0.2 ml of leuprolide is used in place of erythromycin.

EXAMPLE 88

The procedure of Example 87 is followed except that the composition is administered rectally either in the form of an ointment or a suppository.

EXAMPLE 89

The procedure of Example 86 is followed except that the composition is applied to the skin, thereby comprising a transdermal preparation.

EXAMPLE 90

The procedure of Example 82 is followed with the following exceptions: The heating step consists of heating the composition for about 45 seconds at about 50° C. and the adjustment of the pH takes place at a different point in the manufacturing process. Following the heating step, the microparticles are separated from the vehicle and about 10% pectin and about 0.1% ascorbic acid are mixed into the composition comprised of the microparticles. During this step, the pH of the product is adjusted to about 7.4 using HCl or NaOH as required. The finished product comprises a nasally or rectally administered medically useful composition.

EXAMPLE 91

The procedure of Example 90 is followed except that 5 mg/ml of lidocaine is used in place of erythromycin.

EXAMPLE 92

The procedure of Example 91 is followed except that the composition is applied to the skin, thereby comprising a transdermal preparation.

EXAMPLE 93

The process of Example 83 is followed except that 10 mgs/ml of ephredrine is used in place of erythromycin.

EXAMPLE 94

The procedure of Example 93 is followed except that the preparation is applied to the skin thereby comprising a transdermal preparation.

It will be understood that the present disclosure has been made only by way of preferred embodiment and that numerous changes in details of construction, combination, and arrangement of parts can be resorted to without departing from the spirit and scope of the invention as hereunder claimed.

What is claimed and sought to be secured by Letters Patent of the United States is:

1. A method of preparing a composition useful as a system to introduce and transport medically useful compositions in the body of mammals;
   said composition comprising particles of a coacervate-based matrix having one or more physiologically-active compound incorporated therein and a coacervative-based encapsulating film surrounding each particle;
   said method comprising forming a mixture of one or more surface active agents, water and one or more physiologically-active compounds to produce a two phase aqueous coacervate composition containing said compound, and emulsifying the composition to produce an aqueous emulsion of coacervate-based matrix particles containing the physiologically-active compound, said coacervate-based matrix comprising water selected from the group consisting of coacervate phase water, equilibrium phase water, and mixtures thereof, and said physiologically-active compound solubilized therein, said particles having an encapsulating coacervate-based film surrounding the particles.

2. The method of claim 1 further including adding an organic solvent to the mixture to form the two phase coacervate composition.

3. The method of claim 2 wherein the organic solvent comprises N-butyl alcohol or a glyceride.

4. The method of claim 1 wherein the surface active agents comprises a composition of a surface active protein and a surface active phospholipid.

5. A method of preparing a composition containing one or more physiologically-active compounds for oral, inhalation, tissue absorptive or parenteral administration to a mammal comprising emulsifying an aqueous solution of water, a polymerized or polymerizable surface active agent, a coacervating agent and a physicologically-active compound to form an aqueous emulsion of coacervate-based matrix particles containing the physiologically-active compound solubilized therein, and bound in the coacervate matrix within a coacervate-based aqueous film containing the polymerized surface active agent wherein said coacervate matrix comprises water selected from the group consisting of coacervate phase water, equilibrium phase water, and mixtures thereof, and said physiologically-active compound solubilized therein.

6. The method of claim 5 further including emulsifying and microemulsifying the composition to form coacervate particles useful for oral administration having a particle size less than about 800 microns.

7. The method of claim 5 wherein the coacervate particles are microemulsified to less than about 1 micron.

8. The method of claim 5 wherein the surface active agent is a polymerized phospholipid.

9. The method of claim 8 wherein the polymerized phospholipid is polymerized lecithin.

10. The method of claim 8 wherein the phospholipid is selected from the group consisting of lecithin, cephalin, isolecithin, sphingomyelin, phosphalidyl serine, phosphatidic acid, phosphatidyl inositol, phosphatidyl choline, and mixtures thereof.

11. The method of claim 5 wherein the coacervate system includes two surface active agents, at least one of which is a polymer having a molecular weight of 300,000 or less.

12. The method of claim 11 wherein the two surface active agents comprise a phospholipid and a surface active protein.

13. The method of claim 12 wherein the two surface active agents comprise lecithin and polymerized albumin.

14. The method of claim 5 further including drying the composition to form a powder capable of being reconstituted by the addition of a physiologically-acceptable liquid.

15. The method of claim 5 wherein the surface active agent is added in monometric form and further including adding a polymerization initiator to said composition, said polymerization initiator capable of and in an amount sufficient to polymerize the surface active agent during processing of said composition.

16. The method of claim 15 wherein the polymerization initiator is 1-ethyl-3-dimethyl-aminopropylcarbodiimide.

17. The method of claim 5 wherein the physiologically-active compound is a peptide.

18. The method of claim 17 wherein the physiologically-active compound is a polypeptide.

19. The method of claim 5 including admixing with the coacervate composition a glyceride selected from the group consisting of a monoglyceride, a diglyceride, a triglyceride, and mixtures thereof; said physiologically-active compound being dissolved or dispersed in the glyceride; said aqueous coacervate-based matrix particles encapsulated in a coacervate-based film encapsulating the glyceride and the physiologically-active compound within the coacervate-based matrix particles, said coacervate-based matrix particles comprising water selected form the group consisting of coacervate phase water, equilibrium phase water, and mixtures thereof, the glyceride, and the physiologically-active compound dissolved or dispersed within the matrix particles.

20. The method of claim 19 wherein the glyceride is a triglyceride having 8 to 18 carbon atoms per each substituted acid chain.

21. A method of introducing a physiologically-active compound into the circulatory system of a mammal comprising having the mammal orally ingest a composition comprising an aqueous coacervate system including water and a surface active agent, said coacervate system including an aqueous emulsion of coacervate-based matrix particles containing the compound solubilized therein; said aqueous coacervate-based matrix comprising water selected from the group consisting of coacervate phase water, equilibrium phase water, and mixtures thereof, and said physiologically-active compound solubilized therein.

22. The method of claim 21 wherein the surface active agent comprises a protein, polymerized protein, phospholipid, polymerized phospholipid, or mixtures thereof.

23. The method of claim 22 wherein the polymerized protein is polymerized albumin.

24. The method of claim 22 wherein the polymerized phospholipid is a polymer of a compound selected from the group consisting of lecithin, cephalin, isolecithin, sphingomyelin, phosphatidyl serine, phosphatidic acid, phosphatidyl inositol, phosphatidyl choline, and mixtures thereof.

25. The method of claim 24 wherein the polymerized phospholipid is polymerized lecithin.

26. The method of claim 21 further including the step of drying the coacervate to form a powder capable of being reconstituted by the addition of a physiologically-acceptable fluid.

27. A method of introduction a drug into the circulatory system of a mammal comprising having the mammal orally ingest a composition comprising an aqueous emulsion of coacervate-based matrix particles containing water, a surface active agent, and a drug solubilized therein; said coacervate system including a coacervate-based matrix containing the drug in aqueous solution; and a coacervate-based film encapsulating the matrix particles, said aqueous coacervate-based matrix particles comprising water selected from the group consisting of coacervate phase water, equilibrium phase water, and mixtures thereof and the drug.

28. The method of claim 27 wherein the drug comprises insulin.

29. The method of claim 27 wherein the drug comprises an atrial peptide.

30. A method of introducing a drug into the circulatory system of a mammal comprising injecting the body of the mammal with a composition comprising an aqueous coacervate composition including water, a surface active agent, and a drug; said coacervate composition including a coacervate-based matrix containing the drug in aqueous solution or aqueous suspension and a film encapsulating the matrix particles; said aqueous matrix particles containing water selected from the group consisting of coacervate phase water, equilibrium phase water, and mixtures thereof, and the drug solubilized or dispersed therein.

31. The method of claim 30 wherein the drug comprises an atrial peptide.

32. A method of preparing a composition containing one or more physiologically-active compounds for oral, tissue absorptive, inhalation, or parenteral administration to a mammal comprising mixing an aqueous solution of water, a surface active agent, a coacervating agent and a physiologically-active compound to form a two phase aqueous coacervate composition containing the physiologically-active compound in one or both of the two-phase bound as particles in a coacervate matrix and within a coacervate-based aqueous film containing the surface active agent, said coacervate-based matrix comprising water selected from the group consisting of coacervate phase water, equilibrium phase water, and mixtures thereof and the physiologically-active compound in solution within the matrix water; separating the particles; and adding a hydrocolloid to the particles in an amount of 2-20% w/v to form a gel-like surface film surrounding the matrix particles containing the physiologically-active compound.

33. The method of claim 32 further including emulsifying and microemulsifying the composition to form coacervate particles useful for oral administration.

34. The method of claim 32 further including emulsifying and microemulsifying the composition to form coacervate particles useful for oral administration having a particle size less than about 10 microns.

35. The method of claim 32 wherein the coacervate particles are microemulsified to less than about 2 microns.

36. The method of claim 32 wherein the coacervate particles are microemulsified to less than about 1 micron.

37. The method of claim 32 wherein the surface active agent is a polymerized phospholipid.

38. The method of claim 32 further including adding an anti-oxidant to the separated particles.

39. A method of introducing a drug into the circulatory system of a mammal comprising having the mammal orally ingest a composition comprising an aqueous coacervate system including water, a surface active agent, and a drug; said coacervate system including a coacervate-based matrix containing the drug and a film encapsulating the matrix particles; said aqueous coacervate-based matrix comprising water selected from the group consisting of coacervate phase water, equilibrium phase water, and mixtures thereof, and the drug in solution within the matrix water; separating the particles; and adding a hydrocolloid to the particles in an amount of 2-20% w/v to form a gel-like surface film surrounding the matrix particles containing the drug.

40. The method of claim 39 wherein the surface active agent comprises a protein, polymerized protein, phospholipid, polymerized phospholipid, or mixtures thereof.

41. The method of claim 39 wherein the drug comprises insulin.

42. The method of claim 39 wherein the drug comprises an atrial peptide.

43. A method of preparing a composition useful as a system to introduce and transport medically useful composition in the body of mammals;
said composition comprising an aqueous emulsion of particles of a coacervate-based matrix having one or more physiologically-active compounds incorporated therein; said coacervate-based matrix comprising water selected from the group consisting of coacervate phase water, equilibrium phase water, and mixtures thereof, said matrix particles including the physiologically-active compound solubilized in the matrix water;
said method comprising forming a mixture of one or more surface active agents, water and one or more physiologically-active compounds to produce a two phase aqueous coacervate composition containing said compounds, and emulsifying the composition under conditions to produce an aqueous emulsion of the coacervate-based matrix particles containing the physiologically-active compound.

44. A method of administering a physiologically-active compound to a mammal comprising topically applying a coacervate composition containing a physiologically-active compound on the skin of a mammal; said coacervate composition comprising an aqueous emulsion of coacervate-based matrix particles, said matrix particles comprising water, selected from the group consisting of coacervate phase water, equilibrium phase water, and mixtures thereof, said matrix particles including the physiologically-active compound solubilized in the matrix water; and applying sound waves to the topically applied coacervate composition to drive the coacervate composition into the skin.

45. A method of maintaining tissue or an organ of a mammal viable, outside of the mammal's body comprising forming a mixture of one or more surface active agents and water to form a two phase aqueous coacervate composition, and emulsifying the composition to form an aqueous emulsion of coacervate-based matrix particles comprising water selected from the group consisting of coacervate phase water, equilibrium phase water, and mixtures thereof, said matrix particles having solubilized within the matrix water, a compound capable of extending the life of the organ when in contact therewith, and contacting the tissue or organ, outside of the mammal's body, with said aqueous emulsion to maintain the visibility of the tissue or organ until said tissue organ is attached to a mammal.

* * * * *